US012788369B2

(12) United States Patent
Misener et al.

(10) Patent No.: US 12,788,369 B2
(45) Date of Patent: Nov. 10, 2026

(54) DOPPLER-BASED VEIN-ARTERY DETECTION FOR VASCULAR ASSESSMENT

(71) Applicant: Bard Access Systems, Inc., Salt Lake City, UT (US)

(72) Inventors: Anthony K. Misener, Bountiful, UT (US); Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 409 days.

(21) Appl. No.: 17/979,564

(22) Filed: Nov. 2, 2022

(65) Prior Publication Data

US 2023/0135562 A1 May 4, 2023

Related U.S. Application Data

(60) Provisional application No. 63/275,223, filed on Nov. 3, 2021.

(51) Int. Cl.

*A61B 8/00* (2006.01)
*A61B 8/02* (2006.01)
*A61B 8/06* (2006.01)

(52) U.S. Cl.

CPC ................ *A61B 8/463* (2013.01); *A61B 8/02* (2013.01); *A61B 8/06* (2013.01); *A61B 8/4254* (2013.01);

(Continued)

(58) Field of Classification Search

None

See application file for complete search history.

(56) References Cited

U.S. PATENT DOCUMENTS 3,697,917 A 10/1972 Orth et al.
5,148,809 A 9/1992 Biegeleisen-Knight et al.

(Continued)

FOREIGN PATENT DOCUMENTS

CN 102871645 A 1/2013
CN 105107067 B 5/2018

(Continued)

OTHER PUBLICATIONS

Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

(Continued)

*Primary Examiner* — Patricia J Park
(74) *Attorney, Agent, or Firm* — Rutan & Tucker LLP

(57) ABSTRACT

An ultrasound-imaging system can include an ultrasound probe, a console, and a display screen. The ultrasound probe includes an array of ultrasonic transducers that, when activated, emit generated ultrasound signals into a patient, receive reflected ultrasound signals from the patient, and convert the reflected ultrasound signals into corresponding electrical signals for processing into ultrasound images. Operations of the system can include detecting one or more black holes within the ultrasound image and identifying each black hole as a vein, an artery or other anatomic element using doppler ultrasound functionality of the ultrasound probe. Operations can also include defining a window for doppler ultrasound operation, and assessing a blood flow rate within blood vessels. Operations can also include rendering notifications atop the ultrasound image pertaining to the identity of the black hole without obstructing the image of black hole.

22 Claims, 7 Drawing Sheets

(52) U.S. Cl.
CPC ............ *A61B 8/4488* (2013.01); *A61B 8/469* (2013.01); *A61B 8/488* (2013.01); *A61B 8/5207* (2013.01); *A61B 8/5223* (2013.01)

(56) References Cited

U.S. PATENT DOCUMENTS

| | | | |
|---|---|---|---|
| 5,181,513 | A | 1/1993 | Touboul et al. |
| 5,325,293 | A | 6/1994 | Dorne |
| 5,349,865 | A | 9/1994 | Kavli et al. |
| 5,441,052 | A | 8/1995 | Miyajima |
| 5,549,554 | A | 8/1996 | Miraki |
| 5,573,529 | A | 11/1996 | Haak et al. |
| 5,758,650 | A | 6/1998 | Miller et al. |
| 5,775,322 | A | 7/1998 | Silverstein et al. |
| 5,879,297 | A | 3/1999 | Haynor et al. |
| 5,897,503 | A | 4/1999 | Lyon et al. |
| 5,908,387 | A | 6/1999 | LeFree et al. |
| 5,967,984 | A | 10/1999 | Chu et al. |
| 5,970,119 | A | 10/1999 | Hofmann |
| 6,004,270 | A | 12/1999 | Urbano et al. |
| 6,019,724 | A | 2/2000 | Gronningsaeter et al. |
| 6,068,599 | A | 5/2000 | Saito et al. |
| 6,074,367 | A | 6/2000 | Hubbell |
| 6,129,668 | A | 10/2000 | Haynor et al. |
| 6,132,379 | A | 10/2000 | Patacsil et al. |
| 6,216,028 | B1 | 4/2001 | Jaynor et al. |
| 6,233,476 | B1 | 5/2001 | Strommer et al. |
| 6,245,018 | B1 | 6/2001 | Lee |
| 6,263,230 | B1 | 7/2001 | Haynor et al. |
| 6,375,615 | B1 | 4/2002 | Flaherty et al. |
| 6,436,043 | B2 | 8/2002 | Bonnefous |
| 6,498,942 | B1 | 12/2002 | Esenaliev et al. |
| 6,503,205 | B2 | 1/2003 | Manor et al. |
| 6,508,769 | B2 | 1/2003 | Bonnefous |
| 6,511,458 | B2 | 1/2003 | Milo et al. |
| 6,524,249 | B2 | 2/2003 | Moehring et al. |
| 6,543,642 | B1 | 4/2003 | Milliorn |
| 6,554,771 | B1 | 4/2003 | Buil et al. |
| 6,592,520 | B1 | 7/2003 | Peszynski et al. |
| 6,592,565 | B2 | 7/2003 | Twardowski |
| 6,601,705 | B2 | 8/2003 | Molina et al. |
| 6,612,992 | B1 | 9/2003 | Hossack et al. |
| 6,613,002 | B1 | 9/2003 | Clark et al. |
| 6,623,431 | B1 | 9/2003 | Sakuma et al. |
| 6,641,538 | B2 | 11/2003 | Nakaya et al. |
| 6,647,135 | B2 | 11/2003 | Bonnefous |
| 6,687,386 | B1 | 2/2004 | Ito et al. |
| 6,733,458 | B1 | 5/2004 | Steins et al. |
| 6,749,569 | B1 | 6/2004 | Pellegretti |
| 6,754,608 | B2 | 6/2004 | Svanerudh et al. |
| 6,755,789 | B2 | 6/2004 | Stringer et al. |
| 6,840,379 | B2 | 1/2005 | Franks-Farah et al. |
| 6,857,196 | B2 | 2/2005 | Dalrymple |
| 6,979,294 | B1 | 12/2005 | Selzer et al. |
| 7,074,187 | B2 | 7/2006 | Selzer et al. |
| 7,244,234 | B2 | 7/2007 | Ridley et al. |
| 7,359,554 | B2 | 4/2008 | Klingensmith et al. |
| 7,534,209 | B2 | 5/2009 | Abend et al. |
| 7,599,730 | B2 | 10/2009 | Hunter et al. |
| 7,637,870 | B2 | 12/2009 | Flaherty et al. |
| 7,681,579 | B2 | 3/2010 | Schwartz |
| 7,691,061 | B2 | 4/2010 | Hirota |
| 7,699,779 | B2 | 4/2010 | Sasaki et al. |
| 7,720,520 | B2 | 5/2010 | Willis |
| 7,727,153 | B2 | 6/2010 | Fritz et al. |
| 7,734,326 | B2 | 6/2010 | Pedain et al. |
| 7,831,449 | B2 | 11/2010 | Ying et al. |
| 7,905,837 | B2 | 3/2011 | Suzuki |
| 7,925,327 | B2 | 4/2011 | Weese |
| 7,927,278 | B2 | 4/2011 | Selzer et al. |
| 8,014,848 | B2 | 9/2011 | Birkenbach et al. |
| 8,038,619 | B2 | 10/2011 | Steinbacher |
| 8,060,181 | B2 | 11/2011 | Rodriguez Ponce et al. |
| 8,075,488 | B2 | 12/2011 | Burton |
| 8,090,427 | B2 | 1/2012 | Eck et al. |
| 8,105,239 | B2 | 1/2012 | Specht |
| 8,172,754 | B2 | 5/2012 | Watanabe et al. |
| 8,175,368 | B2 | 5/2012 | Sathyanarayana |
| 8,200,313 | B1 | 6/2012 | Rambod et al. |
| 8,211,023 | B2 | 7/2012 | Swan et al. |
| 8,228,347 | B2 | 7/2012 | Beasley et al. |
| 8,298,147 | B2 | 10/2012 | Huennekens et al. |
| 8,303,505 | B2 | 11/2012 | Webler et al. |
| 8,323,202 | B2 | 12/2012 | Roschak et al. |
| 8,328,727 | B2 | 12/2012 | Miele et al. |
| 8,336,536 | B1 | 12/2012 | Wood-Putnam et al. |
| 8,388,541 | B2 | 3/2013 | Messerly et al. |
| 8,409,103 | B2 | 4/2013 | Grunwald et al. |
| 8,449,465 | B2 | 5/2013 | Nair et al. |
| 8,553,954 | B2 | 10/2013 | Saikia |
| 8,556,815 | B2 | 10/2013 | Pelissier et al. |
| 8,585,600 | B2 | 11/2013 | Liu et al. |
| 8,622,913 | B2 | 1/2014 | Dentinger et al. |
| 8,706,457 | B2 | 4/2014 | Hart et al. |
| 8,727,988 | B2 | 5/2014 | Flaherty et al. |
| 8,734,357 | B2 | 5/2014 | Taylor |
| 8,744,211 | B2 | 6/2014 | Owen |
| 8,754,865 | B2 | 6/2014 | Merritt et al. |
| 8,764,663 | B2 | 7/2014 | Smok et al. |
| 8,781,194 | B2 | 7/2014 | Malek et al. |
| 8,781,555 | B2 | 7/2014 | Burnside et al. |
| 8,790,263 | B2 * | 7/2014 | Randall .................... A61B 8/08 600/440 |
| 8,849,382 | B2 | 9/2014 | Cox et al. |
| 8,939,908 | B2 | 1/2015 | Suzuki et al. |
| 8,961,420 | B2 | 2/2015 | Zhang |
| 9,022,940 | B2 | 5/2015 | Meier |
| 9,087,147 | B1 | 7/2015 | Fonte |
| 9,138,290 | B2 | 9/2015 | Hadjicostis |
| 9,199,082 | B1 | 12/2015 | Yared et al. |
| 9,204,858 | B2 | 12/2015 | Pelissier et al. |
| 9,220,477 | B2 | 12/2015 | Urabe et al. |
| 9,295,447 | B2 | 3/2016 | Shah |
| 9,320,493 | B2 | 4/2016 | Visveshwara |
| 9,357,980 | B2 | 6/2016 | Toji et al. |
| 9,364,171 | B2 | 6/2016 | Harris et al. |
| 9,427,207 | B2 | 8/2016 | Sheldon et al. |
| 9,445,780 | B2 | 9/2016 | Hossack et al. |
| 9,456,766 | B2 | 10/2016 | Cox et al. |
| 9,456,804 | B2 | 10/2016 | Tamada |
| 9,468,413 | B2 | 10/2016 | Hall et al. |
| 9,492,097 | B2 | 11/2016 | Wilkes et al. |
| 9,521,961 | B2 | 12/2016 | Silverstein et al. |
| 9,554,716 | B2 | 1/2017 | Burnside et al. |
| 9,582,876 | B2 | 2/2017 | Specht |
| 9,610,061 | B2 | 4/2017 | Ebbini et al. |
| 9,636,031 | B2 | 5/2017 | Cox |
| 9,649,037 | B2 | 5/2017 | Lowe et al. |
| 9,649,048 | B2 | 5/2017 | Cox et al. |
| 9,702,969 | B2 | 7/2017 | Hope Simpson et al. |
| 9,715,757 | B2 | 7/2017 | Ng et al. |
| 9,717,415 | B2 | 8/2017 | Cohen et al. |
| 9,731,066 | B2 | 8/2017 | Liu et al. |
| 9,814,433 | B2 | 11/2017 | Benishti et al. |
| 9,814,531 | B2 | 11/2017 | Yagi et al. |
| 9,861,337 | B2 | 1/2018 | Patwardhan et al. |
| 9,895,138 | B2 | 2/2018 | Sasaki |
| 9,913,605 | B2 | 3/2018 | Harris et al. |
| 9,949,720 | B2 | 4/2018 | Southard et al. |
| 10,043,272 | B2 | 8/2018 | Forzoni et al. |
| 10,449,330 | B2 | 10/2019 | Newman et al. |
| 10,524,691 | B2 | 1/2020 | Newman et al. |
| 10,751,509 | B2 | 8/2020 | Misener |
| 11,564,861 | B1 | 1/2023 | Gaines |
| 11,844,656 | B2 | 12/2023 | Urabe et al. |
| 11,900,593 | B2 | 2/2024 | Dhatt et al. |
| 12,082,976 | B2 | 9/2024 | Urabe et al. |
| 2002/0038088 | A1 | 3/2002 | Imran et al. |
| 2003/0047126 | A1 | 3/2003 | Tomaschko |
| 2003/0106825 | A1 | 6/2003 | Molina et al. |
| 2003/0109910 | A1 | 6/2003 | Lachenbruch et al. |
| 2003/0120154 | A1 | 6/2003 | Sauer et al. |
| 2003/0125629 | A1 | 7/2003 | Ustuner |
| 2003/0135115 | A1 | 7/2003 | Burdette et al. |

(56) References Cited

U.S. PATENT DOCUMENTS

2003/0149366 A1 8/2003 Stringer et al.
2003/0167030 A1 9/2003 Weitzel et al.
2003/0216648 A1 11/2003 Lizzi et al.
2004/0015080 A1 1/2004 Kelly et al.
2004/0055925 A1 3/2004 Franks-Farah et al.
2004/0197267 A1 10/2004 Black et al.
2005/0000975 A1 1/2005 Carco et al.
2005/0049504 A1 3/2005 Lo et al.
2005/0075597 A1 4/2005 Vournakis et al.
2005/0165299 A1 7/2005 Kressy et al.
2005/0251030 A1 11/2005 Azar et al.
2005/0267365 A1 12/2005 Sokulin et al.
2006/0004290 A1 1/2006 Smith et al.
2006/0013523 A1 1/2006 Childlers et al.
2006/0015039 A1 1/2006 Cassidy et al.
2006/0020204 A1 1/2006 Serra et al.
2006/0047617 A1 3/2006 Bacioiu et al.
2006/0079781 A1 4/2006 Germond-Rouet et al.
2006/0184029 A1 8/2006 Haim et al.
2006/0210130 A1 9/2006 Germond-Rouet et al.
2006/0241463 A1 10/2006 Shau et al.
2007/0043341 A1 2/2007 Anderson et al.
2007/0049822 A1 3/2007 Bunce et al.
2007/0073155 A1 3/2007 Park et al.
2007/0167738 A1 7/2007 Timinger et al.
2007/0199848 A1 8/2007 Ellswood et al.
2007/0239005 A1 10/2007 Ogasawara
2007/0239120 A1 10/2007 Brock et al.
2007/0249911 A1 10/2007 Simon
2007/0287886 A1 12/2007 Saadat
2008/0021322 A1 1/2008 Stone et al.
2008/0033293 A1 2/2008 Beasley et al.
2008/0033759 A1 2/2008 Finlay
2008/0051657 A1 2/2008 Rold
2008/0108930 A1 5/2008 Weitzel et al.
2008/0125651 A1 5/2008 Watanabe et al.
2008/0146915 A1 6/2008 McMorrow
2008/0177186 A1 7/2008 Slater et al.
2008/0221425 A1 9/2008 Olson et al.
2008/0269605 A1 10/2008 Nakaya
2008/0294037 A1 11/2008 Richter
2008/0300491 A1 12/2008 Bonde et al.
2009/0012399 A1 1/2009 Sunagawa et al.
2009/0012401 A1 1/2009 Steinbacher
2009/0074280 A1 3/2009 Lu et al.
2009/0105594 A1 4/2009 Reynolds et al.
2009/0118612 A1 5/2009 Grunwald et al.
2009/0124903 A1 5/2009 Osaka
2009/0137887 A1 5/2009 Shariati et al.
2009/0137907 A1 5/2009 Takimoto et al.
2009/0143672 A1 6/2009 Harms et al.
2009/0143684 A1 6/2009 Cermak et al.
2009/0156926 A1 6/2009 Messerly et al.
2009/0171205 A1 7/2009 Kharin et al.
2009/0281413 A1 11/2009 Boyden et al.
2009/0306509 A1 12/2009 Pedersen et al.
2010/0010348 A1 1/2010 Halmann
2010/0168576 A1 7/2010 Poland et al.
2010/0211026 A2 8/2010 Sheetz et al.
2010/0249598 A1 9/2010 Smith et al.
2010/0286515 A1 11/2010 Gravenstein et al.
2010/0298705 A1 11/2010 Pelissier et al.
2010/0312121 A1 12/2010 Guan
2010/0324423 A1 12/2010 El-Aklouk et al.
2011/0002518 A1 1/2011 Ziv-Ari et al.
2011/0026796 A1 2/2011 Hyun et al.
2011/0071404 A1 3/2011 Schmitt et al.
2011/0074244 A1 3/2011 Osawa
2011/0087107 A1 4/2011 Lindekugel et al.
2011/0137173 A1 6/2011 Lowe et al.
2011/0166451 A1 7/2011 Blaivas et al.
2011/0282188 A1 11/2011 Burnside et al.
2011/0295108 A1 12/2011 Cox et al.
2011/0313293 A1 12/2011 Lindekugel et al.
2012/0136242 A1 5/2012 Qi et al.
2012/0136256 A1 5/2012 Nozaki et al.
2012/0143029 A1 6/2012 Silverstein et al.
2012/0165679 A1 6/2012 Orome et al.
2012/0179038 A1 7/2012 Meurer et al.
2012/0179042 A1 7/2012 Fukumoto et al.
2012/0179044 A1 7/2012 Chiang et al.
2012/0197132 A1 8/2012 O'Connor
2012/0220865 A1 8/2012 Brown et al.
2012/0277576 A1 11/2012 Lui
2013/0041250 A1 2/2013 Pelissier et al.
2013/0102889 A1 4/2013 Southard et al.
2013/0131499 A1 5/2013 Chan et al.
2013/0131502 A1 5/2013 Blaivas et al.
2013/0144166 A1 6/2013 Specht et al.
2013/0150724 A1 6/2013 Blaivas et al.
2013/0188832 A1 7/2013 Ma et al.
2013/0197367 A1* 8/2013 Smok .................... A61B 8/085 600/454
2013/0218024 A1 8/2013 Boctor et al.
2013/0323700 A1 12/2013 Samosky et al.
2013/0338503 A1 12/2013 Cohen et al.
2013/0338508 A1 12/2013 Nakamura et al.
2013/0345566 A1 12/2013 Weitzel et al.
2014/0005530 A1 1/2014 Liu et al.
2014/0031694 A1 1/2014 Solek
2014/0066779 A1 3/2014 Nakanishi
2014/0073976 A1 3/2014 Fonte et al.
2014/0100440 A1 4/2014 Cheline et al.
2014/0114194 A1 4/2014 Kanayama et al.
2014/0170620 A1* 6/2014 Savitsky ................ A61B 8/466 434/262
2014/0180098 A1 6/2014 Flaherty et al.
2014/0180116 A1 6/2014 Lindekugel et al.
2014/0188133 A1 7/2014 Misener
2014/0188440 A1 7/2014 Donhowe et al.
2014/0276048 A1 9/2014 Kiley et al.
2014/0276059 A1 9/2014 Sheehan
2014/0276069 A1 9/2014 Amble et al.
2014/0276081 A1 9/2014 Tegels
2014/0276085 A1 9/2014 Miller
2014/0276690 A1 9/2014 Grace
2014/0296694 A1 10/2014 Jaworski
2014/0343431 A1 11/2014 Vajinepalli et al.
2014/0357994 A1 12/2014 Jin et al.
2015/0005738 A1 1/2015 Blacker
2015/0011887 A1 1/2015 Ahn et al.
2015/0011900 A1 1/2015 Lu et al.
2015/0065916 A1 3/2015 Maguire et al.
2015/0073279 A1 3/2015 Cai et al.
2015/0080740 A1 3/2015 Hao et al.
2015/0112200 A1 4/2015 Oberg et al.
2015/0141821 A1* 5/2015 Yoshikawa ............ A61B 8/469 600/438
2015/0190111 A1 7/2015 Fry
2015/0209003 A1 7/2015 Halmann et al.
2015/0209113 A1 7/2015 Burkholz et al.
2015/0209510 A1 7/2015 Burkholz et al.
2015/0209526 A1 7/2015 Matsubara et al.
2015/0245820 A1 9/2015 Tamada
2015/0257735 A1 9/2015 Ball et al.
2015/0272448 A1 10/2015 Fonte et al.
2015/0282890 A1 10/2015 Cohen et al.
2015/0294497 A1 10/2015 Ng et al.
2015/0297097 A1 10/2015 Matsubara et al.
2015/0342572 A1 12/2015 Tahmasebi Maraghoosh et al.
2015/0359520 A1 12/2015 Shan et al.
2015/0359991 A1 12/2015 Dunbar et al.
2016/0000367 A1 1/2016 Lyon
2016/0000399 A1 1/2016 Halmann et al.
2016/0026894 A1 1/2016 Nagase
2016/0029995 A1 2/2016 Navratil et al.
2016/0038119 A1 2/2016 Desjardins
2016/0081674 A1 3/2016 Bagwan et al.
2016/0113517 A1 4/2016 Lee et al.
2016/0113699 A1 4/2016 Sverdlik et al.
2016/0120607 A1 5/2016 Sorotzkin et al.
2016/0125639 A1 5/2016 Park et al.
2016/0157831 A1 6/2016 Kang et al.
2016/0166232 A1 6/2016 Merritt

(56) References Cited

U.S. PATENT DOCUMENTS

2016/0202053 A1 7/2016 Walker et al.
2016/0211045 A1 7/2016 Jeon et al.
2016/0213398 A1 7/2016 Liu
2016/0220124 A1* 8/2016 Grady ................ A61B 5/02028
2016/0259992 A1 9/2016 Knodt et al.
2016/0278869 A1 9/2016 Grunwald
2016/0287214 A1 10/2016 Ralovich et al.
2016/0296208 A1 10/2016 Sethuraman et al.
2016/0374644 A1 12/2016 Mauldin, Jr. et al.
2017/0014105 A1 1/2017 Chono
2017/0020561 A1 1/2017 Cox et al.
2017/0079548 A1 3/2017 Silverstein et al.
2017/0086785 A1 3/2017 Bjaerum
2017/0090571 A1 3/2017 Bjaerum et al.
2017/0103534 A1 4/2017 Park et al.
2017/0143312 A1 5/2017 Hedlund et al.
2017/0157339 A1 6/2017 Li et al.
2017/0164923 A1 6/2017 Matsumoto
2017/0172666 A1 6/2017 Govari et al.
2017/0215842 A1 8/2017 Ryu et al.
2017/0231553 A1 8/2017 Igarashi et al.
2017/0252004 A1 9/2017 Broad et al.
2017/0258522 A1 9/2017 Goshgarian et al.
2017/0259013 A1 9/2017 Boyden et al.
2017/0262982 A1 9/2017 Pagoulatos et al.
2017/0328751 A1 11/2017 Lemke
2017/0367678 A1 12/2017 Sirtori et al.
2018/0015256 A1 1/2018 Southard et al.
2018/0028110 A1 2/2018 Goldman et al.
2018/0116723 A1 5/2018 Hettrick et al.
2018/0125450 A1 5/2018 Blackbourne et al.
2018/0161502 A1 6/2018 Nanan et al.
2018/0199914 A1 7/2018 Ramachandran et al.
2018/0214119 A1 8/2018 Mehrmohammadi et al.
2018/0228465 A1 8/2018 Southard et al.
2018/0235649 A1 8/2018 Elkadi
2018/0235709 A1 8/2018 Donhowe et al.
2018/0289927 A1 10/2018 Messerly
2018/0296185 A1 10/2018 Cox et al.
2018/0310955 A1 11/2018 Lindekugel et al.
2018/0333135 A1 11/2018 Kim et al.
2018/0344293 A1 12/2018 Raju et al.
2019/0029636 A1 1/2019 Lee et al.
2019/0060001 A1 2/2019 Kohli et al.
2019/0060014 A1 2/2019 Hazelton et al.
2019/0090855 A1* 3/2019 Kobayashi ........... A61B 8/5261
2019/0125210 A1 5/2019 Govari et al.
2019/0200951 A1 7/2019 Meier
2019/0239848 A1 8/2019 Bedi et al.
2019/0239850 A1* 8/2019 Dalvin ................. A61B 8/4245
2019/0307419 A1 10/2019 Durfee
2019/0307515 A1 10/2019 Naito et al.
2019/0307516 A1 10/2019 Schotzko et al.
2019/0365347 A1 12/2019 Abe
2019/0365348 A1 12/2019 Toume et al.
2019/0365354 A1* 12/2019 Du ....................... A61B 8/5284
2019/0380676 A1 12/2019 Swan et al.
2020/0027210 A1 1/2020 Haemel et al.
2020/0069929 A1 3/2020 Mason et al.
2020/0085381 A1 3/2020 Weine et al.
2020/0107596 A1 4/2020 Caruso et al.
2020/0113540 A1 4/2020 Gijsbers et al.
2020/0163654 A1 5/2020 Satir et al.
2020/0200900 A1 6/2020 Asami et al.
2020/0229795 A1 7/2020 Tadross et al.
2020/0230391 A1 7/2020 Burkholz et al.
2020/0237403 A1 7/2020 Southard et al.
2020/0238403 A1 7/2020 Ahn et al.
2020/0281563 A1 9/2020 Muller et al.
2020/0359990 A1 11/2020 Poland et al.
2020/0390416 A1 12/2020 Swan et al.
2021/0045716 A1 2/2021 Shiran et al.
2021/0059639 A1 3/2021 Howell
2021/0077058 A1 3/2021 Mashood et al.
2021/0093383 A1 4/2021 Wang et al.
2021/0137492 A1* 5/2021 Imai ..................... A61B 8/4254
2021/0146167 A1 5/2021 Barthe et al.
2021/0161510 A1 6/2021 Sasaki et al.
2021/0186467 A1 6/2021 Urabe et al.
2021/0212658 A1 7/2021 McGrath et al.
2021/0212668 A1 7/2021 Li et al.
2021/0267569 A1 9/2021 Yamamoto
2021/0267570 A1 9/2021 Ulman et al.
2021/0295048 A1 9/2021 Buras et al.
2021/0315538 A1 10/2021 Brandl et al.
2021/0373602 A1 12/2021 Min
2021/0378627 A1 12/2021 Yarmush et al.
2022/0019313 A1 1/2022 He et al.
2022/0022969 A1 1/2022 Misener
2022/0039777 A1 2/2022 Durfee
2022/0039829 A1 2/2022 Zijlstra et al.
2022/0071593 A1 3/2022 Tran
2022/0096053 A1 3/2022 Sethuraman et al.
2022/0096797 A1 3/2022 Prince
2022/0101980 A1 3/2022 Rothenberg et al.
2022/0104791 A1 4/2022 Matsumoto
2022/0104886 A1 4/2022 Blanchard et al.
2022/0117582 A1 4/2022 McLaughlin et al.
2022/0160434 A1 5/2022 Messerly et al.
2022/0168050 A1 6/2022 Sowards et al.
2022/0172354 A1 6/2022 Misener et al.
2022/0225963 A1 7/2022 Sutton et al.
2022/0233346 A1 7/2022 McElya
2022/0296303 A1 9/2022 McLeod et al.
2022/0304652 A1 9/2022 Peterson et al.
2022/0330922 A1 10/2022 Sowards et al.
2022/0334251 A1 10/2022 Sowards et al.
2022/0338833 A1 10/2022 Dhatt et al.
2022/0361840 A1 11/2022 Matsumoto et al.
2022/0406460 A1 12/2022 Golan et al.
2023/0044620 A1 2/2023 Shochat et al.
2023/0048327 A1 2/2023 Lampe et al.
2023/0107629 A1 4/2023 Sowards et al.
2023/0113291 A1 4/2023 de Wild et al.
2023/0132148 A1 4/2023 Sowards et al.
2023/0135757 A1 5/2023 Bauer et al.
2023/0138970 A1 5/2023 Sowards et al.
2023/0148872 A1 5/2023 Sowards et al.
2023/0201539 A1 6/2023 Howell
2023/0277153 A1 9/2023 Sowards et al.
2023/0277154 A1 9/2023 Sowards et al.
2023/0293143 A1 9/2023 Sowards et al.
2023/0298757 A1 9/2023 Golan et al.
2023/0338010 A1 10/2023 Sturm
2023/0371928 A1 11/2023 Rajguru et al.
2023/0381472 A1 11/2023 Chisena et al.
2023/0397900 A1 12/2023 Prince
2024/0065673 A1 2/2024 Sowards et al.
2024/0197403 A1 6/2024 Mino et al.
2024/0307024 A1 9/2024 Sowards et al.
2025/0017559 A1 1/2025 Denny et al.
2025/0057501 A1 2/2025 Prince
2025/0104238 A1 3/2025 Misener et al.
2025/0177060 A1 6/2025 Messerly et al.
2025/0186026 A1 6/2025 Tran
2025/0251511 A1 8/2025 Sowards et al.
2025/0352167 A1 11/2025 Sowards et al.
2026/0123906 A1 5/2026 Sowards et al.

FOREIGN PATENT DOCUMENTS

EP 0933063 A1 8/1999
EP 1504713 A1 2/2005
EP 1591074 B1 5/2008
EP 2823766 A1 1/2015
EP 3181083 A1 6/2017
EP 3870059 9/2021
JP 2000271136 A 10/2000
JP 2007222291 A 9/2007
JP 2014150928 A 8/2014
JP 2018175547 A 11/2018
KR 20180070878 A 6/2018
KR 102176196 B1 11/2020
WO 2004082749 A2 9/2004

(56) References Cited

FOREIGN PATENT DOCUMENTS

| | | | |
|---|---|---|---|
| WO | 2007115174 | A2 | 10/2007 |
| WO | 2010029521 | A2 | 3/2010 |
| WO | 2010076808 | A1 | 7/2010 |
| WO | 2013059714 | A1 | 4/2013 |
| WO | 2014/115150 | A1 | 7/2014 |
| WO | 2015/017270 | A1 | 2/2015 |
| WO | 2016081023 | A1 | 5/2016 |
| WO | 2017096487 | A1 | 6/2017 |
| WO | 2017214428 | A1 | 12/2017 |
| WO | 2018/026878 | A1 | 2/2018 |
| WO | 2018134726 | A1 | 7/2018 |
| WO | 2018138343 | A1 | 8/2018 |
| WO | 2019/232451 | A1 | 12/2019 |
| WO | 2020/002620 | A1 | 1/2020 |
| WO | 2020/016018 | A1 | 1/2020 |
| WO | 2019/232454 | A9 | 2/2020 |
| WO | 2020/044769 | A1 | 3/2020 |
| WO | 2020067897 | A1 | 4/2020 |
| WO | 2020083660 | A1 | 4/2020 |
| WO | 2020/186198 | A1 | 9/2020 |
| WO | 2021123905 | A2 | 6/2021 |
| WO | 2021198226 | A1 | 10/2021 |
| WO | 2022/072727 | A2 | 4/2022 |
| WO | 2022/081904 | A1 | 4/2022 |
| WO | 2022069208 | A1 | 4/2022 |
| WO | 2022/119853 | A1 | 6/2022 |
| WO | 2022115479 | A1 | 6/2022 |
| WO | 2022119856 | A1 | 6/2022 |
| WO | 2022221703 | A1 | 10/2022 |
| WO | 2022221714 | A1 | 10/2022 |
| WO | 2023059512 | A1 | 4/2023 |
| WO | 2023076268 | A1 | 5/2023 |
| WO | 2023081220 | A1 | 5/2023 |
| WO | 2023081223 | A1 | 5/2023 |
| WO | 2023091424 | A1 | 5/2023 |
| WO | 2023167866 | A1 | 9/2023 |
| WO | 2023177718 | A1 | 9/2023 |
| WO | 2024044277 | A1 | 2/2024 |
| WO | 2024180503 | A1 | 9/2024 |
| WO | 2025/015198 | A1 | 1/2025 |

OTHER PUBLICATIONS

Pagoulatos, N. et al. "New spatial localizer based on fiber optics with applications in 3D ultrasound imaging" Proceeding of Spie, vol. 3976 (Apr. 18, 2000; Apr. 18, 2000).

PCT/US2021/049294 filed Sep. 7, 2021 International Search Report and Written Opinion dated Dec. 8, 2021.

PCT/US2021/049712 filed Sep. 9, 2021 International Search Report and Written Opinion dated Dec. 14, 2021.

PCT/US2021/060622 filed Nov. 23, 2021 International Search Report and Written Opinion dated Mar. 3, 2022.

PCT/US2021/061267 filed Nov. 30, 2021 International Search Report and Written Opinion dated Mar. 9, 2022.

PCT/US2021/061276 filed Nov. 30, 2021 International Search Report and Written Opinion dated Mar. 9, 2022.

PCT/US2022/025082 filed Apr. 15, 2022 International Search Report and Written Opinion dated Jul. 11, 2022.

PCT/US2022/025097 filed Apr. 15, 2022 International Search Report and Written Opinion dated Jul. 8, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

U.S. Appl. No. 15/650,474, filed Jul. 14, 2017 Final Office Action dated Jun. 2, 2020.

U.S. Appl. No. 15/650,474, filed Jul. 14, 2017 Non-Final Office Action dated Dec. 16, 2019.

U.S. Appl. No. 15/650,474, filed Jul. 14, 2017 Notice of Allowance dated Dec. 11, 2020.

U.S. Appl. No. 15/650,474, filed Jul. 14, 2017 Notice of Allowance dated Mar. 1, 2021.

U.S. Appl. No. 17/020,476, filed Sep. 14, 2020 Advisory Action dated Aug. 19, 2022.

U.S. Appl. No. 17/020,476, filed Sep. 14, 2020 Final Office Action dated Jun. 9, 2022.

U.S. Appl. No. 17/020,476, filed Sep. 14, 2020 Non-Final Office Action dated Feb. 9, 2022.

U.S. Appl. No. 17/020,476, filed Sep. 14, 2020 Non-Final Office Action dated Sep. 23, 2022.

U.S. Appl. No. 17/471,015, filed Sep. 9, 2021 Non-Final Office Action dated Aug. 16, 2022.

William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

U.S. Appl. No. 17/468,318, filed Sep. 7, 2021 Notice of Allowance dated Jan. 18, 2024.

U.S. Appl. No. 17/471,015, filed Sep. 9, 2021 Advisory Action dated Feb. 2, 2024.

U.S. Appl. No. 17/534,099, filed Nov. 23, 2021 Advisory Action dated Dec. 8, 2023.

U.S. Appl. No. 17/538,943, filed Nov. 30, 2021 Non-Final Office Action dated Jan. 30, 2024.

U.S. Appl. No. 17/684,180, filed Mar. 1, 2022 Final Office Action dated Jan. 18, 2024.

U.S. Appl. No. 17/722,111, filed Apr. 15, 2022 Non-Final Office Action dated Dec. 22, 2023.

U.S. Appl. No. 17/722,151, filed Apr. 15, 2022 Advisory Action dated Jan. 2, 2024.

U.S. Appl. No. 17/894,460, filed Aug. 24, 2022 Final Office Action dated Jan. 31, 2024.

PCT/US2023/014143 filed Feb. 28, 2023 International Search Report and Written Opinion dated Jun. 12, 2023.

PCT/US2023/015266 filed Mar. 15, 2023 International Search Report and Written Opinion dated May 25, 2023.

U.S. Appl. No. 17/684,180, filed Mar. 1, 2022 Non-Final Office Action dated Jul. 28, 2023.

EP 20866520.8 filed Apr. 5, 2022 Extended European Search Report dated Aug. 22, 2023.

PCT/US2022/025097 filed Apr. 15, 2021 International Preliminary Report on Patentability dated Oct. 26, 2023.

PCT/US2023/030970 filed Aug. 23, 2023 International Search Report and Written Opinion dated Oct. 30, 2023.

U.S. Appl. No. 17/468,318, filed Sep. 7, 2021 Advisory Action dated Nov. 6, 2023.

U.S. Appl. No. 17/468,318, filed Sep. 7, 2021 Final Office Action dated Sep. 8, 2023.

U.S. Appl. No. 17/471,015, filed Sep. 9, 2021 Final Office Action dated Oct. 12, 2023.

U.S. Appl. No. 17/534,099, filed Nov. 23, 2021 Final Office Action dated Sep. 29, 2023.

U.S. Appl. No. 17/538,911, filed Nov. 30, 2021 Advisory Action dated Nov. 22, 2023.

U.S. Appl. No. 17/538,911, filed Nov. 30, 2021 Final Office Action dated Sep. 13, 2023.

U.S. Appl. No. 17/722,151, filed Apr. 15, 2022 Final Office Action dated Nov. 6, 2023.

U.S. Appl. No. 17/722,151, filed Apr. 15, 2022 Non-Final Office Action dated Sep. 7, 2023.

U.S. Appl. No. 17/894,460, filed Aug. 24, 2022 Non-Final Office Action dated Nov. 6, 2023.

PCT/US2022/048716 filed Nov. 2, 2022 International Search Report and Written Opinion dated Feb. 24, 2023.

PCT/US2022/048722 filed Nov. 2, 2022 International Search Report and Written Opinion dated Feb. 24, 2023.

PCT/US2022/049983 filed Nov. 15, 2022 International Search Report and Written Opinion dated Mar. 29, 2023.

PCT/US2022/047727 filed Oct. 25, 2022 International Search Report and Written Opinion dated Jan. 25, 2023.

Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.

(56) References Cited

OTHER PUBLICATIONS

U.S. Appl. No. 17/020,476, filed Sep. 14, 2020 Final Office Action dated Jan. 5, 2023.
U.S. Appl. No. 17/020,476, filed Sep. 14, 2020 Notice of Allowance dated Apr. 28, 2022.
U.S. Appl. No. 17/468,318, filed Sep. 7, 2021 Non-Final Office Action dated Apr. 12, 2023.
U.S. Appl. No. 17/471,015, filed Sep. 9, 2021 Non-Final Office Action dated Mar. 30, 2023.
U.S. Appl. No. 17/534,099, filed Nov. 23, 2021 Non-Final Office Action dated Mar. 31, 2023.
U.S. Appl. No. 17/538,911, filed Nov. 30, 2021 Non-Final Office Action dated Mar. 2, 2023.
U.S. Appl. No. 17/684,180, filed Mar. 1, 2022 Restriction Requirement dated May 19, 2023.
M. Ikhsan, K. K. Tan, AS. Putra, C. F. Kong, et al., "Automatic identification of blood vessel cross-section for central venous catheter placement using a cascading classifier," 39th Annual International Conference of the IEEE Engineering in Medicine and Biology Society (EMBC). pp. 1489-1492 (Year: 2017).
PCT/US2022/045372 filed Sep. 30, 2022 International Search Report and Written Opinion dated Jan. 14, 2023.
U.S. Appl. No. 17/471,015, filed Sep. 9, 2021 Non-Final Office Action dated Mar. 28, 2024.
U.S. Appl. No. 17/534,099, filed Nov. 23, 2021 Non-Final Office Action dated Mar. 14, 2024.
U.S. Appl. No. 17/538,911, filed Nov. 30, 2021 Notice of Allowance dated Mar. 14, 2024.
U.S. Appl. No. 17/538,943, filed Nov. 30, 2021 Notice of Allowance dated Aug. 14, 2024.
U.S. Appl. No. 17/684,180, filed Mar. 1, 2022 Advisory Action dated Apr. 4, 2024.
U.S. Appl. No. 17/684,180, filed Mar. 1, 2022 Non-Final Office Action dated May 8, 2024.
U.S. Appl. No. 17/722,111, filed Apr. 15, 2022 Final Office Action dated Jul. 12, 2024.
U.S. Appl. No. 17/722,151, filed Apr. 15, 2022 Non-Final Office Action dated Mar. 25, 2024.
U.S. Appl. No. 17/894,460, filed Aug. 24, 2022 Advisory Action dated Apr. 4, 2024.
U.S. Appl. No. 17/957,562, filed Sep. 30, 2022 Non-Final Office Action dated Jun. 20, 2024.
U.S. Appl. No. 17/979,601, filed Nov. 2, 2022 Non-Final Office Action dated Aug. 20, 2024.
U.S. Appl. No. 18/238,281, filed Aug. 25, 2023 Non-Final Office Action dated Mar. 22, 2024.
U.S. Appl. No. 18/238,281, filed Aug. 25, 2023 Notice of Allowance dated Jul. 16, 2024.
U.S. Appl. No. 17/684,180, filed Mar. 1, 2022 Advisory Action dated Dec. 27, 2024.
U.S. Appl. No. 17/684,180, filed Mar. 1, 2022 Non-Final Office Action dated Jan. 17, 2025.
U.S. Appl. No. 17/722,111, filed Apr. 15, 2022 Notice of Allowance dated Dec. 18, 2024.
U.S. Appl. No. 17/722,151, filed Apr. 15, 2022 Advisory Action dated Dec. 27, 2024.
U.S. Appl. No. 17/894,460, filed Aug. 24, 2022 Final Office Action dated Dec. 31, 2024.
U.S. Appl. No. 17/957,562, filed Sep. 30, 2022 Advisory Action dated Feb. 12, 2025.
U.S. Appl. No. 17/973,171, filed Oct. 25, 2022 Non-Final Office Action dated Dec. 6, 2024.
U.S. Appl. No. 17/979,601, filed Nov. 2, 2022 Advisory Action dated Feb. 11, 2025.
U.S. Appl. No. 17/979,601, filed Nov. 2, 2022 Final Office Action dated Dec. 5, 2024.
U.S. Appl. No. 17/987,698, filed Nov. 15, 2022 Advisory Action dated Feb. 21, 2025.
U.S. Appl. No. 17/987,698, filed Nov. 15, 2022 Final Office Action dated Dec. 13, 2024.
U.S. Appl. No. 18/121,802, filed Mar. 15, 2023 Non-Final Office Action dated Dec. 16, 2024.
U.S. Appl. No. 18/674,601, filed May 24, 2024 Non-Final Office Action dated Jan. 7, 2025.
PCT/US2024/037647 filed Jul. 11, 2024 International Search Report and Written Opinion dated Oct. 16, 2024.
Thermographic venous blood flow characterization with external cooling stimulation (Year: 2018).
U.S. Appl. No. 17/471,015, filed Sep. 9, 2021 Notice of Allowance dated Oct. 29, 2024.
U.S. Appl. No. 17/534,099, filed Nov. 23, 2021 Notice of Allowance dated Sep. 18, 2024.
U.S. Appl. No. 17/684,180, filed Mar. 1, 2022 Final Office Action dated Sep. 23, 2024.
U.S. Appl. No. 17/722,111, filed Apr. 15, 2022 Advisory Action dated Oct. 23, 2024.
U.S. Appl. No. 17/722,151, filed Apr. 15, 2022 Final Office Action dated Sep. 20, 2024.
U.S. Appl. No. 17/894,460, filed Aug. 24, 2022 Non-Final Office Action dated Sep. 25, 2024.
U.S. Appl. No. 17/957,562, filed Sep. 30, 2022 Final Office Action dated Nov. 27, 2024.
U.S. Appl. No. 17/987,698, filed Nov. 15, 2022 Non-Final Office Action dated Sep. 20, 2024.
U.S. Appl. No. 18/113,003, filed Feb. 22, 2023 Non-Final Office Action dated Nov. 27, 2024.
U.S. Appl. No. 17/722,151, filed Apr. 15, 2022 Non-Final Office Action dated Dec. 23, 2025.
U.S. Appl. No. 17/894,460, filed Aug. 24, 2022 Non-Final Office Action dated Jan. 14, 2026.
U.S. Appl. No. 17/973,171, filed Oct. 25, 2022 Examiner's Answer dated Jan. 28, 2026.
U.S. Appl. No. 17/987,698, filed Nov. 15, 2022 Non-Final Office Action dated Mar. 16, 2026.
U.S. Appl. No. 19/042,983, filed Jan. 31, 2025 Notice of Allowance dated Feb. 24, 2026.
Chen et al.,3D near infrared and ultrasound imaging of peripheral blood vessels for real-time localization and needle guidance. InMedical Image Computing and Computer-Assisted Intervention—MICCAI 2016 (pp. 388-396) (Year: 2016).
Konica Minolta, "Vascular NAVI" product website. https://www.konicaminolta.com/global-en/healthcare/technology/ultrasound/vascularnavi/index.html. Last accessed Jun. 2025.
U.S. Appl. No. 17/684,180, filed Mar. 1, 2022 Advisory Action dated Aug. 22, 2025.
U.S. Appl. No. 17/722,151, filed Apr. 15, 2022 Final Office Action dated Jul. 11, 2025.
U.S. Appl. No. 17/957,562, filed Sep. 30, 2022 Examiner's Answer dated Jun. 16, 2025.
U.S. Appl. No. 17/973,171, filed Oct. 25, 2022 Advisory Action dated Jun. 30, 2025.
U.S. Appl. No. 18/113,003, filed Feb. 22, 2023 Advisory Action dated Jul. 2, 2025.
U.S. Appl. No. 18/113,003, filed Feb. 22, 2023 Notice of Allowance dated Aug. 15, 2025.
U.S. Appl. No. 18/121,802, filed Mar. 15, 2023 Notice of Allowance dated Jun. 5, 2025.
U.S. Appl. No. 18/221,318, filed Jul. 12, 2023 Non-Final Office Action dated Jun. 23, 2025.
U.S. Appl. No. 17/684,180, filed Mar. 1, 2022 Final Office Action dated May 29, 2025.
U.S. Appl. No. 17/722,151, filed Apr. 15, 2022 Non-Final Office Action dated Mar. 21, 2025.
U.S. Appl. No. 17/894,460, filed Aug. 24, 2022 Advisory Action dated Mar. 13, 2025.
U.S. Appl. No. 17/973,171, filed Oct. 25, 2022 Final Office Action dated Apr. 3, 2025.
U.S. Appl. No. 17/979,601, filed Nov. 2, 2022 Notice of Allowance dated Mar. 27, 2025.
U.S. Appl. No. 17/987,698, filed Nov. 15, 2022 Non-Final Office Action dated May 23, 2025.
U.S. Appl. No. 18/113,003, filed Feb. 22, 2023 Final Office Action dated Apr. 29, 2025.

(56) References Cited

OTHER PUBLICATIONS

U.S. Appl. No. 18/221,318, filed Jul. 12, 2023 Restriction Requirement dated Mar. 28, 2025.
U.S. Appl. No. 18/674,601, filed May 24, 2024 Notice of Allowance dated Mar. 26, 2025.
U.S. Appl. No. 17/684,180, filed Mar. 1, 2022 Notice of Allowance dated Sep. 30, 2025.
U.S. Appl. No. 17/722,151, filed Apr. 15, 2022 Advisory Action dated Oct. 16, 2025.
U.S. Appl. No. 17/894,460, filed Aug. 24, 2022 Examiner's Answer dated Oct. 2, 2025.
U.S. Appl. No. 17/987,698, filed Nov. 15, 2022 Advisory Action dated Nov. 21, 2025.
U.S. Appl. No. 17/987,698, filed Nov. 15, 2022 Final Office Action dated Sep. 12, 2025.
U.S. Appl. No. 18/221,318, filed Jul. 12, 2023 Final Office Action dated Oct. 14, 2025.
U.S. Appl. No. 18/936,351, filed Nov. 4, 2024 Non-Final Office Action dated Nov. 10, 2025.
Sonka, Momodou L., T. Campbell Arnold, and Ivan A. Kuznetsov. "Machine learning in point of care ultrasound." POCUS journal 7. Kidney (2022): 78. (Year: 2022).
U.S. Appl. No. 17/722,151 filed Apr. 15, 2022 Notice of Allowance dated Jun. 9, 2026.
U.S. Appl. No. 17/957,562, filed Sep. 30, 2022 Board Decision dated Apr. 22, 2026.
U.S. Appl. No. 17/957,562, filed Sep. 30, 2022 Notice of Allowance dated May 1, 2026.
U.S. Appl. No. 17/987,698, filed Nov. 15, 2022 Final Office Action dated Jun. 25, 2026.
U.S. Appl. No. 18/221,318, filed Jul. 12, 2023 Non-Final Office Action dated May 6, 2026.
U.S. Appl. No. 18/936,351, filed Nov. 4, 2024 Notice of Allowance dated Jun. 10, 2026.
U.S. Appl. No. 19/058,331, filed Feb. 20, 2025 Notice of Allowance dated Apr. 20, 2026.
U.S. Appl. No. 19/251,382, filed Jun. 26, 2025 Restriction Requirement dated May 18, 2026.

* cited by examiner

DOPPLER-BASED VEIN-ARTERY DETECTION FOR VASCULAR ASSESSMENT

PRIORITY

This application claims the benefit of priority to U.S. Provisional Application No. 63/275,223, filed Nov. 3, 2021, which is incorporated by reference in its entirety into this application.

BACKGROUND

Ultrasound imaging is a widely accepted tool for guiding interventional instruments such as needles to targets such as blood vessels or organs in the human body. In order to successfully guide, for example, a needle to a blood vessel using ultrasound imaging, the needle is monitored in real-time both immediately before and after a percutaneous puncture in order to enable a clinician to determine the distance and the orientation of the needle to the blood vessel and ensure successful access thereto. However, through inadvertent movement of an ultrasound probe during the ultrasound imaging, the clinician can lose both the blood vessel and the needle, which can be difficult and time consuming to find again. In addition, it is often easier to monitor the distance and orientation of the needle immediately before the percutaneous puncture with a needle plane including the needle perpendicular to an image plane of the ultrasound probe. And it is often easier to monitor the distance and orientation of the needle immediately after the percutaneous puncture with the needle plane parallel to the image plane. As with inadvertently moving the ultrasound probe, the clinician can lose both the blood vessel and the needle when adjusting the image plane before and after the percutaneous puncture, which can be difficult and time consuming to find again. What is needed are ultrasound-imaging systems and methods thereof that can dynamically adjust the image plane to facilitate guiding interventional instruments to targets in at least the human body.

Doppler ultrasound is a noninvasive approach to estimating the blood flow through your blood vessels by bouncing high-frequency sound waves (ultrasound) off circulating red blood cells. A doppler ultrasound can estimate how fast blood flows by measuring the rate of change in its pitch (frequency). During a doppler ultrasound, a technician trained in ultrasound imaging (sonographer) positions an ultrasound probe against the skin over a predefined area. Doppler ultrasound may be performed as an alternative to more-invasive procedures, such as angiography, which involves injecting dye into the blood vessels so that they show up clearly on X-ray images.

A Doppler ultrasound may help diagnose many conditions, including blood clots, poorly functioning valves in your leg veins, which can cause blood or other fluids to pool in your legs (venous insufficiency), heart valve defects and congenital heart disease, a blocked artery (arterial occlusion), decreased blood circulation into your legs (peripheral artery disease), bulging arteries (aneurysms), and narrowing of an artery, such as in your neck (carotid artery stenosis)

Doppler ultrasound may also detect a direction of blood flow. For example, doppler ultrasound can differentiate an artery from a vein since the direction of blood flow within an artery is generally in the opposite direction from a blood flow within an adjacent vein. As doppler ultrasound applies to blood flow, ultrasound images that include doppler ultrasound commonly portray results in a manner that obstructs the visibility of the blood vessel thereby causing difficulty in visualizing an image of a medical device in relation to the blood vessel.

Disclosed herein are systems and methods providing visual notifications pertaining to doppler ultrasound that for identifying a blood vessel within an ultrasound image based on doppler ultrasound and providing visual notification pertaining to doppler ultrasound results that maintain visibility of the cross-sectional area of the blood vessel.

SUMMARY

Disclosed herein is an ultrasound-imaging system including, in some embodiments, an ultrasound probe, a console, and a display screen. The ultrasound probe includes an array of ultrasonic transducers, where activated ultrasonic transducers of the array of ultrasonic transducers are configured to emit generated ultrasound signals into a patient, receive reflected ultrasound signals from the patient, and convert the reflected ultrasound signals into corresponding electrical signals of the ultrasound signals for processing into ultrasound image data and doppler ultrasound data. The console is configured to communicate with the ultrasound probe, and the console includes one or more processors and a non-transitory computer-readable medium having stored thereon logic that, when executed by the one or more processors, causes system operations.

The operations include: (i) detecting a black hole within a predefined target area of the patient based on ultrasound image data, (ii) determining a blood flow condition within the black hole based at least partially on doppler ultrasound data, (iii) defining an ultrasound image of the predefined target area including an image of the black hole, and (iv) superimposing a notification atop the ultrasound image, where the notification indicates the direction of blood flow with respect to the image of the black hole, In some embodiments, the operations further include determining a direction of blood flow within the black hole with respect to an image plane of the ultrasound image, and the notification indicates the direction of blood flow with respect to the image of the black hole In some embodiments, the operations further include rendering the ultrasound image on a display coupled with the system.

In some embodiments, the notification does not obstruct the image of the black hole. In further embodiments, the operations further include defining a boundary surrounding the image of the black hole and superimposing the notification outside of the boundary.

The operations my further include identifying the blood vessel as a vein or alternatively as an artery, where identifying the blood vessel as a vein or an artery is based at least partially on the condition of the blood flow within the blood vessel.

The operations my further include identifying the blood vessel as a vein or alternatively as an artery, based at least partially on the direction of the blood flow with respect to the image plane.

In some embodiments, the doppler ultrasound data includes a measurement of a pulsatility of the blood flow, and identifying the blood vessel as a vein or an artery is based at least partially on the pulsatility measurement.

In some embodiments, the operations further include: (i) comparing the ultrasound image with one or more corresponding ultrasound images stored in memory, where the comparison including a comparison of spatial positioning of the black hole within the ultrasound image, and (ii) at least partially as a result of the comparison, identifying the blood vessel as a vein or an artery. The notification may indicate the identity of the blood vessel as a vein or an artery and the notification may further indicate a confidence for the identification of the blood vessel.

In some embodiments, the operations further include measuring a blood flow rate within the black hole, comparing the blood flow rate with a range of blood flow rates stored in memory and as a result of the comparison, determining that the blood flow rate within the blood vessel is compromised. The operations may further include, as a result of the comparison, determining that the blood vessel is partially and/or totally occluded.

In some embodiments, the operations further include: (i) obtaining a first blood flow rate measurement for the blood vessel, (ii) obtaining a second blood flow rate measurement for the blood vessel, the second measurement subsequent to the first measurement, (iii) comparing the second measurement with the first measurement, and (iv) as a result of the flow rate measurement comparison, determining that the blood flow rate within the blood vessel is compromised.

In some embodiments, the operations further include detecting a plurality of black holes within the predefined target area of the patient based on ultrasound image data, determining a blood flow condition within each of the black holes based at least partially on doppler ultrasound data, and identifying each of the black holes as a blood vessel or alternatively as one or more nerves, where identifying the black hole as one or more nerves includes determining a non-flow condition of blood within the respective black hole.

The operations may further include defining a doppler ultrasound window extending at least partially across the ultrasound image and determining the blood flow condition within each of the one or more black holes encompassed by the doppler ultrasound window. In some embodiments, defining the doppler ultrasound window includes detecting the one or more black holes based on the ultrasound image data, and automatically defining the doppler ultrasound window to encompass the one or more black holes.

In some embodiments, defining the doppler ultrasound window includes receiving an input via an input device of the system, and defining the doppler ultrasound window based on the input, where the input includes a selected portion of the ultrasound image.

In some embodiments, the ultrasound probe further includes an array of magnetic sensors configured to convert magnetic signals from a magnetized medical device into corresponding electrical signals of the magnetic signals for processing by the processor into distance and orientation information with respect to the predefined target area for rendering of an iconographic representation of the medical device atop the ultrasound image. In further embodiments, defining the doppler ultrasound window includes defining the doppler ultrasound window based on a position of the iconographic representation of the medical device atop the ultrasound image.

Disclosed herein also is method of an ultrasound-imaging system including a non-transitory computer-readable medium ("CRM") having executable logic that cause the ultrasound-imaging system to perform a set of operations for ultrasound imaging when the logic is executed by a processor of a console of the ultrasound-imaging system, where the method includes performing the operations described above.

These and other features of the concepts provided herein will become more apparent to those of skill in the art in view of the accompanying drawings and following description, which describe particular embodiments of such concepts in greater detail.

DRAWINGS

DESCRIPTION

Figure 1:
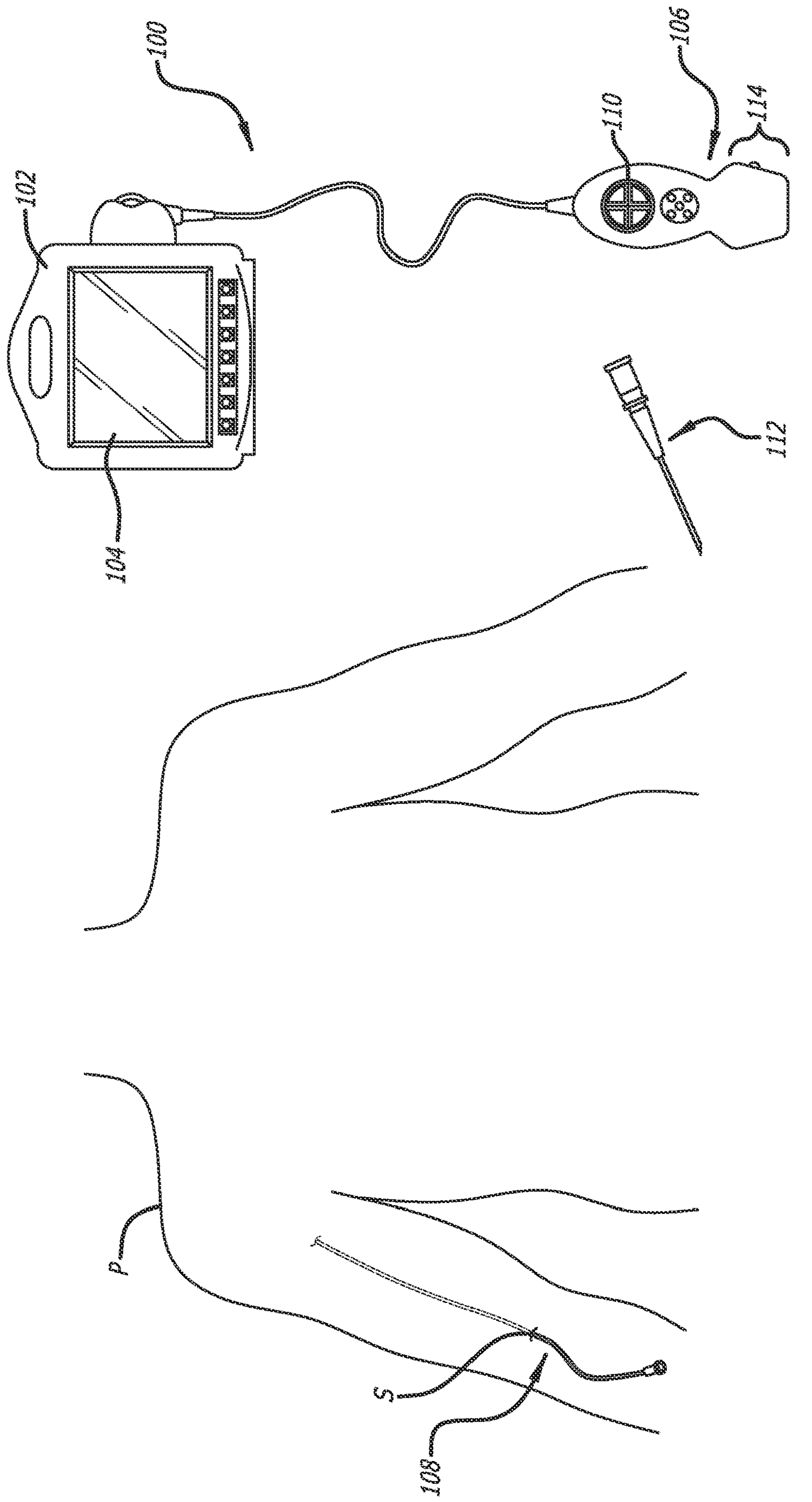
FIG. 1 illustrates an ultrasound-imaging system and a patient in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Ultrasound-Imaging Systems

Figure 2:
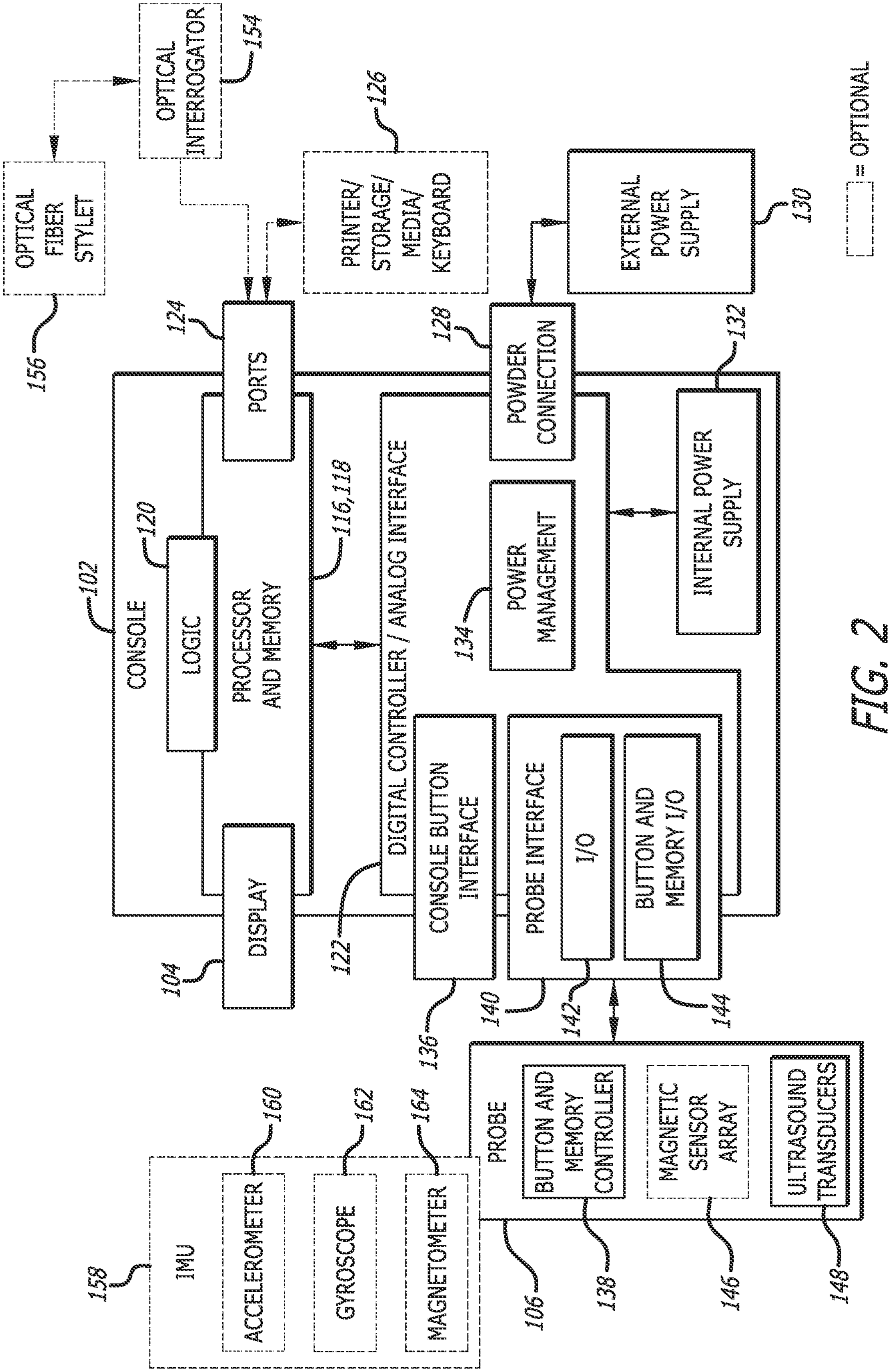
FIG. 2 illustrates a block diagram of a console of the ultrasound-imaging system of FIG. 1 in accordance with some embodiments.
Figure 3B:
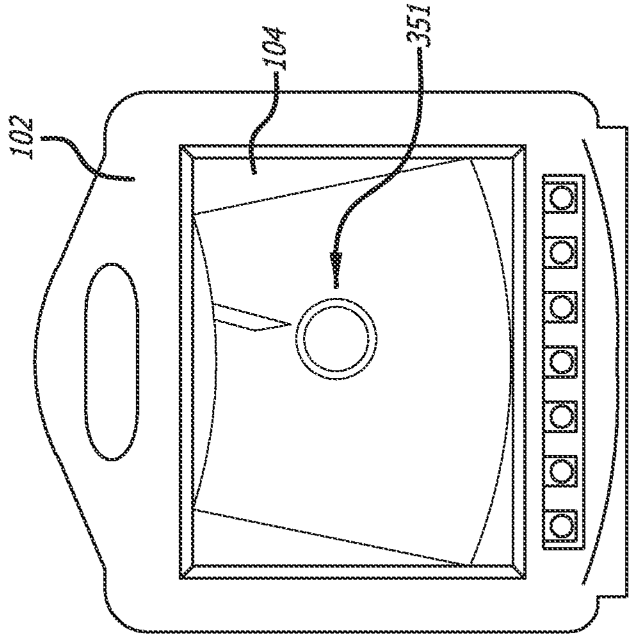
FIG. 3B illustrates an ultrasound image of the blood vessel of FIG. 3A on a display screen of the ultrasound-imaging system in accordance with some embodiments.
Figure 3A:
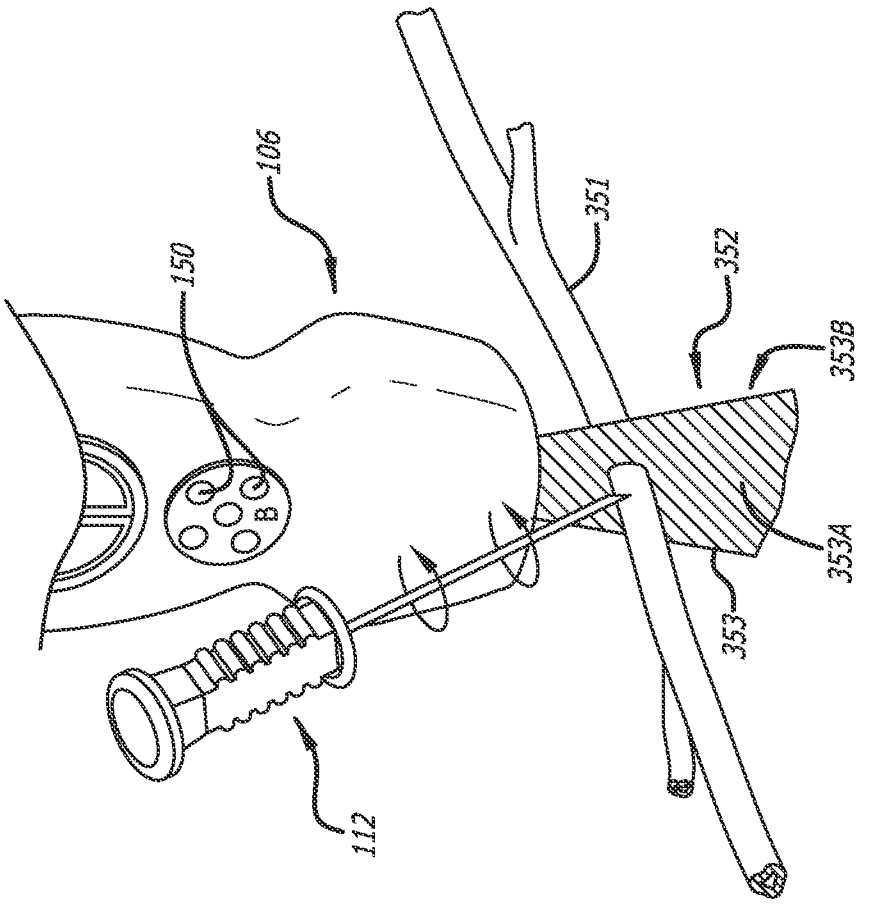
FIG. 3A illustrates an ultrasound probe of the ultrasound-imaging system imaging a blood vessel in accordance with some embodiments.

FIG. 1 illustrates an ultrasound-imaging system 100, a needle 112, and a patient P in accordance with some embodiments. FIG. 2 illustrates a block diagram of the ultrasound-imaging system 100 in accordance with some embodiments. FIG. 3A illustrates an ultrasound probe 106 of the ultrasound-imaging system 100 imaging a blood vessel of the patient P prior to accessing the blood vessel in accordance with some embodiments. FIG. 3B illustrates an ultrasound image of the blood vessel of FIG. 3A on a display screen 104 of the ultrasound-imaging system 100 with an iconographic representation of the needle 112 in accordance with some embodiments.

As shown, the ultrasound-imaging system 100 includes a console 102, the display screen 104, and the ultrasound probe 106. The ultrasound-imaging system 100 is useful for imaging a target such as a blood vessel or an organ within a body of the patient P prior to a percutaneous puncture with the needle 112 for inserting the needle 112 or another medical device into the target and accessing the target. Indeed, the ultrasound-imaging system 100 is shown in FIG. 1 in a general relationship to the patient P during an ultrasound-based medical procedure to place a catheter 108 into the vasculature of the patient P through a skin insertion site S created by a percutaneous puncture with the needle 112. It should be appreciated that the ultrasound-imaging system 100 can be useful in a variety of ultrasound-based medical procedures other than catheterization. For example, the percutaneous puncture with the needle 112 can be performed to biopsy tissue of an organ of the patient P.

The console 102 houses a variety of components of the ultrasound-imaging system 100, and it is appreciated the console 102 can take any of a variety of forms. A processor 116 and memory 118 such as random-access memory ("RAM") or non-volatile memory (e.g., electrically erasable programmable read-only memory ["EEPROM"]) is included in the console 102 for controlling functions of the ultrasound-imaging system 100, as well as executing various logic operations or algorithms during operation of the ultrasound-imaging system 100 in accordance with executable logic 120 therefor stored in the memory 118 for execution by the processor 116. For example, the console 102 is configured to instantiate by way of the logic 120 one or more processes for dynamically adjusting a distance of activated ultrasonic transducers 149 from a predefined target area (e.g., an area including a blood vessel), an orientation of the activated ultrasonic transducers 149 to the predefined target area, or both the distance and the orientation of the activated ultrasonic transducers 149 with respect to the predefined target area, as well as process electrical signals from the ultrasound probe 106 into ultrasound images. Dynamically adjusting the activated ultrasonic transducers 149 uses ultrasound-imaging data, magnetic-field data, shape-sensing data, or a combination thereof received by the console 102 for activating certain ultrasonic transducers of a 2-D array of the ultrasonic transducers 148 or moving those already activated in a linear array of the ultrasonic transducers 148. A digital controller/analog interface 122 is also included with the console 102 and is in communication with both the processor 116 and other system components to govern interfacing between the ultrasound probe 106 and other system components set forth herein.

The ultrasound-imaging system 100 further includes ports 124 for connection with additional components such as optional components 126 including a printer, storage media, keyboard, etc. The ports 124 can be universal serial bus ("USB") ports, though other types of ports can be used for this connection or any other connections shown or described herein. A power connection 128 is included with the console 102 to enable operable connection to an external power supply 130. An internal power supply 132 (e.g., a battery) can also be employed either with or exclusive of the external power supply 130. Power management circuitry 134 is included with the digital controller/analog interface 122 of the console 102 to regulate power use and distribution.

Optionally, a stand-alone optical interrogator 154 can be communicatively coupled to the console 102 by way of one of the ports 124. Alternatively, the console 102 can include an integrated optical interrogator integrated into the console 102. Such an optical interrogator is configured to emit input optical signals into a companion optical-fiber stylet 156 for shape sensing with the ultrasound-imaging system 100, which optical-fiber stylet 156, in turn, is configured to be inserted into a lumen of a medical device such as the needle 112, and convey the input optical signals from the optical interrogator 154 to a number of FBG sensors along a length of the optical-fiber stylet 156. The optical interrogator 154 is also configured to receive reflected optical signals conveyed by the optical-fiber stylet 156 reflected from the number of FBG sensors, the reflected optical signals indicative of a shape of the optical-fiber stylet 156. The optical interrogator 154 is also configured to convert the reflected optical signals into corresponding electrical signals for processing by the console 102 into distance and orientation information with respect to the target for dynamically adjusting a distance of the activated ultrasonic transducers 149, an orientation of the activated ultrasonic transducers 149, or both the distance and the orientation of the activated ultrasonic transducers 149 with respect to the target or the medical device when it is brought into proximity of the target. For example, the distance and orientation of the activated ultrasonic transducers 149 can be adjusted with respect to a blood vessel as the target. Indeed, an image plane can be established by the activated ultrasonic transducers 149 being perpendicular or parallel to the blood vessel in accordance with an orientation of the blood vessel. The distance and orientation information can also be used for displaying an iconographic representation of the medical device on the display.

The display screen 104 is integrated into the console 102 to provide a GUI and display information for a clinician during such as one-or-more ultrasound images of the target area of the patient P attained by the ultrasound probe 106. In addition, the ultrasound-imaging system 100 enables the distance and orientation of a magnetized medical device such as the needle 112 to be superimposed in real-time atop an ultrasound image of the target, thus enabling a clinician to accurately guide the magnetized medical device to an intended target. Notwithstanding the foregoing, the display screen 104 can alternatively be separate from the console 102 and communicatively coupled thereto. A console button interface 136 and control buttons 110 (see FIG. 1) included on the ultrasound probe 106 can be used to immediately call up a desired mode to the display screen 104 by the clinician for assistance in an ultrasound-based medical procedure. In some embodiments, the display screen 104 is an LCD device.

The ultrasound probe 106 is employed in connection with ultrasound-based visualization of a target such as a blood vessel (see FIG. 3A) in preparation for inserting the needle 112 or another medical device into the target. Such visualization gives real-time ultrasound guidance and assists in reducing complications typically associated with such insertion, including inadvertent arterial puncture, hematoma, pneumothorax, etc. As described in more detail below, the ultrasound probe 106 is configured to provide to the console 102 electrical signals corresponding to both the ultrasound-imaging data, the magnetic-field data, the shape-sensing data, or a combination thereof for the real-time ultrasound guidance.

Figure 4:
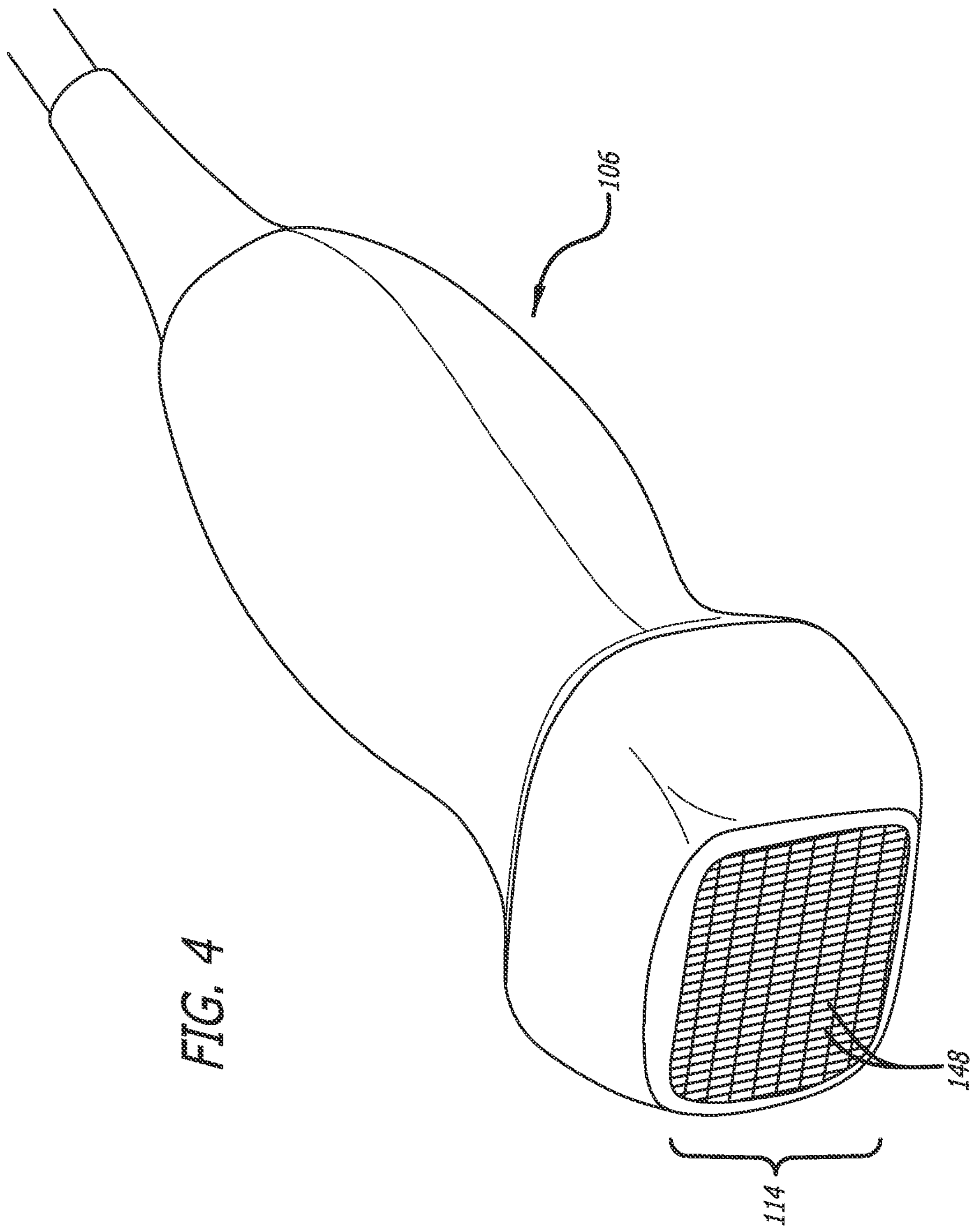
FIG. 4 illustrates the ultrasound probe of the ultrasound-imaging system configured as a 2-D ultrasound probe in accordance with some embodiments.

FIG. 4 illustrates the ultrasound probe 106 of the ultrasound-imaging system 100 configured as a 2-D ultrasound probe 106 in accordance with some embodiments. The ultrasound probe 106 includes a probe head 114 that houses a mounted and moveable (e.g., translatable or rotatable along a central axis) linear array of the ultrasonic transducers 148 or a 2-D array of the ultrasonic transducers 148, wherein the ultrasonic transducers 148 are piezoelectric transducers or capacitive micromachined ultrasonic transducers ("CMUTs"). When the ultrasound probe 106 is configured with the 2-D array of the ultrasonic transducers 148, a subset of the ultrasonic transducers 148 is linearly activated as needed for ultrasound imaging in accordance with ultrasound-imaging data, magnetic-field data, shape-sensing data, or a combination thereof to maintain the target in an image plane or switch to a different image plane (e.g., from perpendicular to a medical-device plane to parallel to the medical-device plane) including the target.

The probe head 114 is configured for placement against skin of the patient P proximate a prospective needle-insertion site where the activated ultrasonic transducers 149 in the probe head 114 can generate and emit the generated ultrasound signals into the patient P in a number of pulses, receive reflected ultrasound signals or ultrasound echoes from the patient P by way of reflection of the generated ultrasonic pulses by the body of the patient P, and convert the reflected ultrasound signals into corresponding electrical signals for processing into ultrasound images by the console 102 to which the ultrasound probe 106 is communicatively coupled. In this way, a clinician can employ the ultrasound-imaging system 100 to determine a suitable insertion site and establish vascular access with the needle 112 or another medical device.

The ultrasound probe 106 further includes the control buttons 110 for controlling certain aspects of the ultrasound-imaging system 100 during an ultrasound-based medical procedure, thus eliminating the need for the clinician to reach out of a sterile field around the patient P to control the ultrasound-imaging system 100. For example, a control button of the control buttons 110 can be configured to select or lock onto the target (e.g., a blood vessel, an organ, etc.) when pressed for visualization of the target in preparation for inserting the needle 112 or another medical device into the target. Such a control button can also be configured to deselect the target, which is useful whether the target was selected by the control button or another means such as by holding the ultrasound probe 106 stationary over the target to select the target, issuing a voice command to select the target, or the like.

FIG. 2 shows that the ultrasound probe 106 further includes a button and memory controller 138 for governing button and ultrasound probe 106 operation. The button and memory controller 138 can include non-volatile memory (e.g., EEPROM). The button and memory controller 138 is in operable communication with a probe interface 140 of the console 102, which includes an input/output ("I/O") component 142 for interfacing with the ultrasonic transducers 148 and a button and memory I/O component 144 for interfacing with the button and memory controller 138.

Also as seen in FIGS. 2 and 3A, the ultrasound probe 106 can include a magnetic-sensor array 146 for detecting a magnetized medical device such as the needle 112 during ultrasound-based medical procedures. The magnetic-sensor array 146 includes a number of magnetic sensors 150 embedded within or included on a housing of the ultrasound probe 106. The magnetic sensors 150 are configured to detect a magnetic field or a disturbance in a magnetic field as magnetic signals associated with the magnetized medical device when it is in proximity to the magnetic-sensor array 146. The magnetic sensors 150 are also configured to convert the magnetic signals from the magnetized medical device (e.g., the needle 112) into electrical signals for the console 102 to process into distance and orientation information for the magnetized medical device with respect to the predefined target, as well as for display of an iconographic representation of the magnetized medical device on the display screen 104. (See the magnetic field B of the needle 112 in FIG. 3A.) Thus, the magnetic-sensor array 146 enables the ultrasound-imaging system 100 to track the needle 112 or the like.

Though configured here as magnetic sensors, it is appreciated that the magnetic sensors 150 can be sensors of other types and configurations. Also, though they are described herein as included with the ultrasound probe 106, the magnetic sensors 150 of the magnetic-sensor array 146 can be included in a component separate from the ultrasound probe 106 such as a sleeve into which the ultrasound probe 106 is inserted or even a separate handheld device. The magnetic sensors 150 can be disposed in an annular configuration about the probe head 114 of the ultrasound probe 106, though it is appreciated that the magnetic sensors 150 can be arranged in other configurations, such as in an arched, planar, or semi-circular arrangement.

Each magnetic sensor of the magnetic sensors 150 includes three orthogonal sensor coils for enabling detection of a magnetic field in three spatial dimensions. Such 3-dimensional ("3-D") magnetic sensors can be purchased, for example, from Honeywell Sensing and Control of Morristown, NJ Further, the magnetic sensors 150 are configured as Hall-effect sensors, though other types of magnetic sensors could be employed. Further, instead of 3-D sensors, a plurality of 1-dimensional ("1-D") magnetic sensors can be included and arranged as desired to achieve 1-, 2-, or 3-D detection capability.

Five magnetic sensors 150 are included in the magnetic-sensor array 146 so as to enable detection of a magnetized medical device such as the needle 112 in three spatial dimensions (e.g., X, Y, Z coordinate space), as well as the pitch and yaw orientation of the magnetized medical device itself. Detection of the magnetized medical device in accordance with the foregoing when the magnetized medical device is brought into proximity of the ultrasound probe 106 allows for dynamically adjusting a distance of the activated ultrasonic transducers 149, an orientation of the activated ultrasonic transducers 149, or both the distance and the orientation of the activated ultrasonic transducers 149 with respect to the target or the magnetized medical device. For example, the distance and orientation of the activated ultrasonic transducers 149 can be adjusted with respect to a blood vessel as the target. Indeed, an image plane can be established by the activated ultrasonic transducers 149 being perpendicular or parallel to the blood vessel in accordance with an orientation of the blood vessel. Note that in some embodiments, orthogonal sensing components of two or more of the magnetic sensors 150 enable the pitch and yaw attitude of the magnetized medical device to be determined, which enables tracking with relatively high accuracy. In other embodiments, fewer than five or more than five magnetic sensors of the magnetic sensors 150 can be employed in the magnetic-sensor array 146. More generally, it is appreciated that the number, size, type, and placement of the magnetic sensors 150 of the magnetic-sensor array 146 can vary from what is explicitly shown here.

As shown in FIG. 2, the ultrasound probe 106 can further include an inertial measurement unit ("IMU") 158 or any one or more components thereof for inertial measurement selected from an accelerometer 160, a gyroscope 162, and a magnetometer 164 configured to provide positional-tracking data of the ultrasound probe 106 to the console 102 for stabilization of an image plane. The processor 116 is further configured to execute the logic 120 for processing the positional-tracking data for adjusting the distance of the activated ultrasonic transducers 149 from the target, the orientation of the activated ultrasonic transducers 149 to the target, or both the distance and the orientation of the activated ultrasonic transducers 149 with respect to the target to maintain the distance and the orientation of the activated ultrasonic transducers 149 with respect to the target when the ultrasound probe 106 is inadvertently moved with respect to the target.

It is appreciated that a medical device of a magnetizable material enables the medical device (e.g., the needle 112) to be magnetized by a magnetizer, if not already magnetized, and tracked by the ultrasound-imaging system 100 when the magnetized medical device is brought into proximity of the magnetic sensors 150 of the magnetic-sensor array 146 or inserted into the body of the patient P during an ultrasound-based medical procedure. Such magnetic-based tracking of the magnetized medical device assists the clinician in placing a distal tip thereof in a desired location, such as in a lumen of a blood vessel, by superimposing a simulated needle image representing the real-time distance and orientation of the needle 112 over an ultrasound image of the body of the patient P being accessed by the magnetized medical device. Such a medical device can be stainless steel such as SS 304 stainless steel; however, other suitable needle materials that are capable of being magnetized can be employed. So configured, the needle 112 or the like can produce a magnetic field or create a magnetic disturbance in a magnetic field detectable as magnetic signals by the magnetic-sensor array 146 of the ultrasound probe 106 so as to enable the distance and orientation of the magnetized medical device to be tracked by the ultrasound-imaging system 100 for dynamically adjusting the distance of the activated ultrasonic transducers 149, an orientation of the activated ultrasonic transducers 149, or both the distance and the orientation of the activated ultrasonic transducers 149 with respect to the magnetized medical device.

During operation of the ultrasound-imaging system 100, the probe head 114 of the ultrasound probe 106 is placed against skin of the patient P. An ultrasound beam 352 is produced so as to ultrasonically image a portion of a target area that may include a blood vessel beneath a surface of the skin of the patient P such as the blood vessel 351 of FIG. 3A. (See FIG. 3A.). The ultrasound beam defines an image plane 353 having a front side 353A consistent with a front side of the ultrasound probe 106 and an opposite facing back side 353B. The ultrasonic image of the blood vessel 351 can be depicted and stabilized on the display screen 104 of the ultrasound-imaging system 100 as shown in FIG. 3B.

Figure 5B:
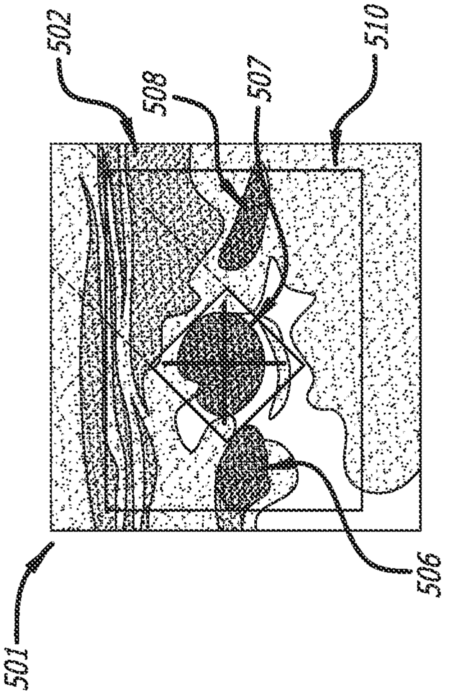
FIG. 5B illustrates an ultrasound image of FIG. 5A further including a doppler ultrasound window in accordance with some embodiments.
Figure 5D:
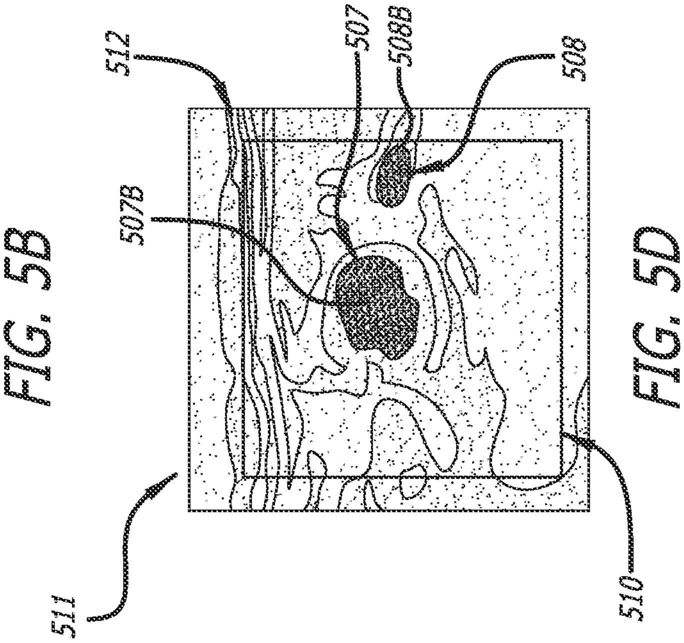
FIG. 5D illustrates an ultrasound image similar to the ultrasound image of FIG. 5C where blood flow through the black holes is compromised in accordance with some embodiments.
Figure 5A:
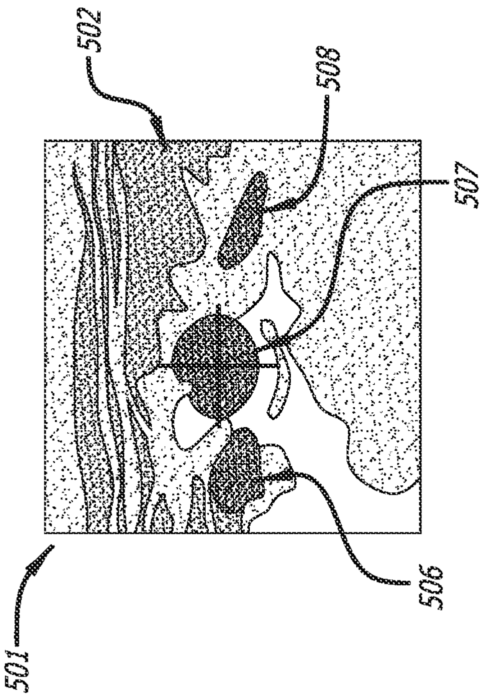
FIG. 5A illustrates an ultrasound image including black holes in accordance with some embodiments.
Figure 5C:
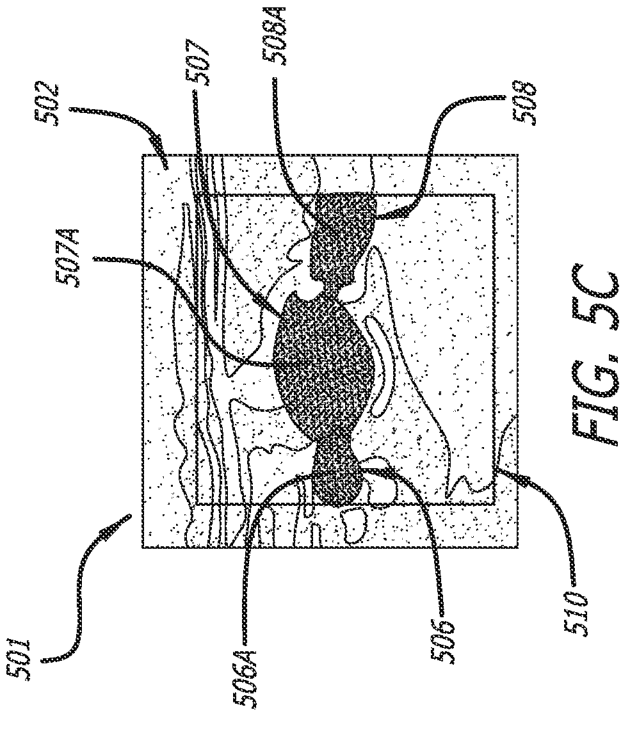
FIG. 5C illustrates an ultrasound image of FIG. 5A indicating blood flow through the black holes in accordance with some embodiments.

FIGS. 5A-5C illustrate an exemplary ultrasound image as may be obtained via the ultrasound probe 106 and as may be rendered the display 104. The ultrasound image 501 includes a predetermined target area 502 of the patient such as a subcutaneous portion of the patient's arm including blood vessels as further described below.

FIG. 5A illustrates the darker areas of the ultrasound image 501 having shapes that indicate specific anatomical structures of the subcutaneous tissue. Herein some darker areas are referred to as black holes, such as the black holes 506, 507, and 508. In some instances, the black holes may indicate blood vessels within the subcutaneous tissue or more specifically, the blood flow area of the blood vessels. In the illustrated embodiment, the logic 120 is configured to identify black holes within the ultrasound image that may be consistent with blood vessels and/or in some embodiments, nerves or nerve bundles. In the illustrated exemplary image 501, the logic 120 has identified the black holes 506, 507, and 508 as blood vessels and as such, the black holes 506, 507, and 508 may be referred to the blood vessels 506, 507, and 508 herein below.

In some embodiments, the logic 120 may identify one of the blood vessels 506, 507, and 508 as a target blood vessel in accordance with a predefined medical procedure. For example, the blood vessel 507 may be identified as a target blood vessel for receiving the needle 112 (see FIGS. 1, 3A). In some embodiments, identifying a black hole as a blood vessel may include comparing the ultrasound image with one or more corresponding ultrasound images stored in memory 118 (see FIG. 1) as further described below.

FIG. 5B further illustrates the ultrasound image 501. The ultrasound probe 106 is configured to detect motion of elements included in the ultrasound image 501 via doppler ultrasound. For example, the ultrasound probe 106 is configured to detect motion consistent with blood flow within the black holes (blood vessels) 506, 507, and 508. As such, the logic 120 may, based at least partially on doppler ultrasound, determine a blood flow within one or more of the black holes 506, 507, and 508 including a direction of the blood flow and, in some embodiments, a blood flow rate.

The logic 120 may further identify the black hole as a vein or alternatively as artery based on the determined direction of the blood flow within the black hole in relation to the image plane 353 of the ultrasound probe 106. For example, in further reference to FIG. 3A, the clinician in some instances may orient the ultrasound probe 106 consistent with a medical procedure, i.e., such that the front side of the ultrasound probe 106 and the corresponding front side 353A of the image plane 353 face upstream in relation to the venous flow. In such an instance, the logic 120 may identify a black hole having blood flow directed into the front side 353A of the image plane 353 as a vein. Conversely, in accordance with the same orientation of the ultrasound probe 106, the logic 120 may identify a black hole having blood flow directed out of the front side 353A of the image plane 353 as an artery.

In some embodiments, alternatively or in addition to direction of the blood flow, the logic 120 may identify a blood vessel as a vein or an artery based on a pulsatility of the blood flow. Typically, arterial blood flow is more pulsatile that venous blood flow. As such, the logic 120 may compare the pulsatility of the blood flow within a given blood vessel/black hole as measured via doppler ultrasound with a pulsatility limit stored in memory 118. In a first instance, where the measured pulsatility exceeds the pulsatility limit, the logic 120 may identify the blood vessel/black hole as an artery. Conversely, in a second instance, where the measured pulsatility is below the pulsatility limit, the logic 120 may identify the blood vessel/black hole as a vein.

In further embodiments, the logic 120 may identify a blood vessel as a vein or an artery based on the pulsatile motion of a blood vessel wall defining a cyclical change in black hole shape or size. In other words, pressure pules within a blood vessel due to pulsatile blood flow therethrough may cause the cross-sectional area (i.e., black hole area) of the blood vessel to expand and contract. As the arterial blood flow is more pulsatile that venous blood flow, the logic 120 may compare a magnitude of cyclical expansion and contraction of the blood vessel wall for a given blood vessel/black hole as measured via doppler ultrasound with an expansion and contraction magnitude limit stored in memory 118. In a first instance, where the measured magnitude of cyclical expansion and contraction exceeds the expansion and contraction magnitude limit, the logic 120 may identify the blood vessel/black hole as an artery. In a second instance, where the measured magnitude of cyclical expansion and contraction is below the expansion and contraction magnitude limit, the logic 120 may identify the blood vessel/black hole as a vein.

Generally, the ultrasound probe 106 may be configured to detect motion (e.g., blood flow) within a doppler ultrasound window 510. The doppler ultrasound window 510 may extend across all or a portion of the ultrasound image 501. In some embodiments, the logic 120 may automatically define the doppler ultrasound window 510 based on identified black holes within the ultrasound image 501. For example, the logic 120 may automatically define the doppler ultrasound window 510 to encompass one or more of the black holes 506, 507, and 508 within the ultrasound image 501.

In some embodiments, the logic 120 may automatically define the doppler ultrasound window 510 based partially on the comparison of the ultrasound image 501 with the corresponding ultrasound images stored in memory 118. For example, the corresponding ultrasound images may include a predefined doppler ultrasound window to be applied to the ultrasound image 501 and the logic 120 may define the doppler ultrasound window 510 according to the predefined doppler ultrasound window.

In some embodiments, the clinician may define the doppler ultrasound window 510 via input to the system 100 via an input device such as a computer mouse or other pointing device. In some embodiments, the input may be facilitated via a GUI interface of the display 104. In other embodiments, the input may be facilitated via the control buttons 110 (see FIG. 1) on the ultrasound probe 106.

FIG. 5C further illustrates the ultrasound image 501. As stated above, the logic 120 may determine motion within the ultrasound window including blood flow with the black holes 506, 507, and 508. The doppler ultrasound process may operate in the background of the ultrasound imaging process. As shown in FIG. 5C, results of the doppler ultrasound process may include a direction of blood flow as illustrated by the direction indications 506A, 507A, and 508A which are shown in FIG. 5C for illustration purposes only, i.e., the direction indications 506A, 507A, and 508A may not be rendered on the display 104 along with the ultrasound image 501 because they obstruct the images of the black holes 506, 507, and 508. The direction indications 506A, 507A, and 508A may be based on the orientation of the image plane 353 (see FIG. 3A). In the illustrated embodiment, the direction indications 506A, 508A indicate a direction of the blood flow into the page (e.g., into the front side 353A of the image plane 353 of FIG. 3A). Conversely, the direction indication 507A indicates a direction of the blood flow out of the page (e.g., out of the front side 353A of the image plane 353 of FIG. 3A).

FIG. 5D further illustrates a second exemplary ultrasound image of a target area 512. In some instances, the target area 512 may be positioned adjacent the target area 502 of FIGS. 5A-5C, such as downstream of the target area 502, for example. In other instances, the target area 512 may be the same as the target area 502 with the ultrasound image 511 having been acquired at a different time than the ultrasound image 501, such as a subsequent time, for example. In the second exemplary image 511, the blood flow through the blood vessels is compromised (i.e., reduced). As shown, the size of the blood vessels 507 and 508 are reduced in relation to the areas of the blood vessels 507 and 508 of FIGS. 501A-501C. According to one example, the size of the black hole 506 of FIGS. 5A-5C is sufficiently reduced so that the logic 120 does not detect the black hole 506 in FIG. 5D. Similar to the FIG. 5C, direction indications 507B and 508B indicate the direction of the blood flow through blood vessels 507 and 508 consistent with the direction indications 507A and 508A of FIG. 5C.

In some embodiments, the logic 120 may compare the image 511 with corresponding images stored in memory 118 and as a result of the comparison determine the that the blood flows through the blood vessels 507 and 508 are reduced according to a size of the black holes. Alternatively, and/or in addition to the comparison of the image 511 with corresponding images stored in memory 118, the logic 120 may determine the reduction in blood flow via doppler ultrasound.

Figure 6:
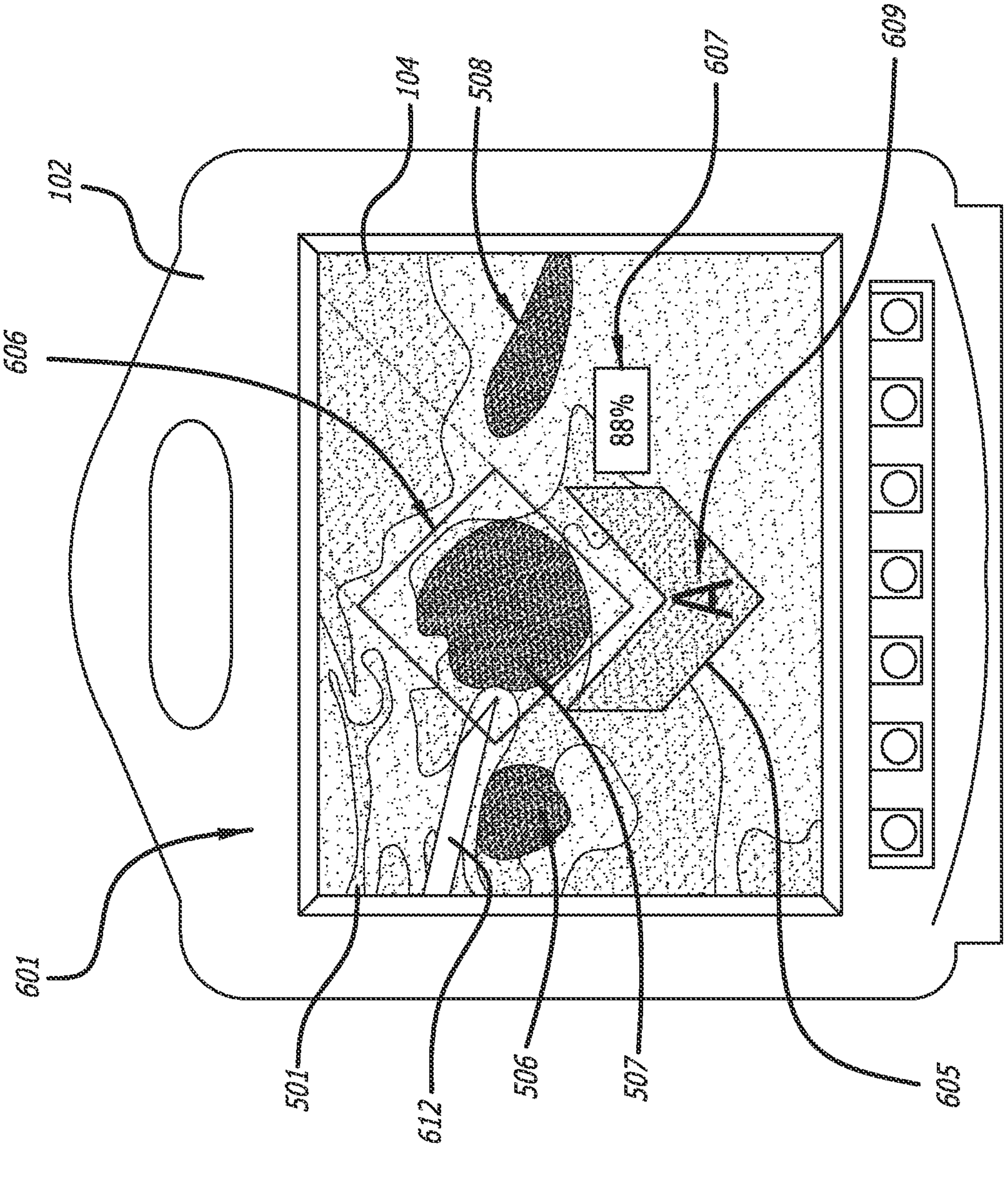
FIG. 6 illustrates an exemplary screenshot of the ultrasound image of the FIG. 5A including notifications superimposed atop the ultrasound in accordance with some embodiments.

FIG. 6 illustrates an exemplary screenshot as may be rendered on the display 104. In the illustrated embodiment, the screenshot 601 includes the ultrasound image 501 and one or more notifications pertaining to the ultrasound image 501. The notifications may include one or more indicia relating to a target blood vessel, such as the blood vessel 507, for example. The notifications may include a condition of the blood flow within the blood vessel. The notifications may more specifically include a target indicium 606 indicating the identified black hole 507 as the target blood vessel pertaining to a defined medical procedure. The target indicium 606 is disposed outside the area of the black hole 507 so as to not obstruct the image of the black hole 507. In some embodiments, the target indicium 606 may include a border extending around the image of the black hole 507.

The notifications include a flow direction indicium 605 indicating the direction of the blood flow in relation to the black hole 507 as depicted in the ultrasound image 501. For example, in an instance where the direction of blood flow is out of the image plane (i.e., out of the screen of the display 104), the flow direction indicium 605 may include an arrow, pointer, or other shape pointing away from the black hole 507 indicating the direction of the blood flow out of the blood vessel 507 as shown in FIG. 6. Alternatively, in an instance where the direction of the blood flow is in the opposite direction, the flow direction indicium 605 may point toward the blood vessel 507. As may be appreciated by one of ordinary skill, the flow direction indicium 605 may include any shape, symbol, word, etc., suitable for indicating the direction of blood flow. In some embodiments, the target indicum 606 and the flow direction indicium 605 may be combined in a single indicum.

The notification may include a black hole identity indicator 609 for indicating the black hole as a vein or an artery. In some embodiments, the notifications may also include a confidence indicator 607 regarding the identification of the black hole 507 as an artery or alternatively as a vein. The confidence indicator 607 may be a number such as a percent probability or any other indicator suitable for communicating a confidence level of the identification.

In some embodiments, the screenshot 601 of the ultrasound image 501 may include an iconographic representation 612 of the needle 112 superimposed atop the ultrasound image 501 in accordance with some embodiments.

Methods

Methods of the foregoing ultrasound-imaging systems include methods implemented in the ultrasound-imaging systems. For example, a method of the ultrasound-imaging system 100 includes a non-transitory CRM (e.g., EEPROM) having the logic 120 stored thereon that causes the ultrasound-imaging system 100 to perform a set of operations for ultrasound imaging when the logic 120 is executed by the processor 116 of the console 102. Such a method may, for description purposes, be referred to herein as activating operations, processing operations, and displaying operations. Any methods disclosed herein comprise one or more steps, actions or operations for performing the described method. The method includes operations (e.g., steps or actions) that may be interchanged with one another. In other words, unless a specific order of the operations is required for proper operation of the embodiment, the order and/or use of specific operations may be modified.

Figure 7:
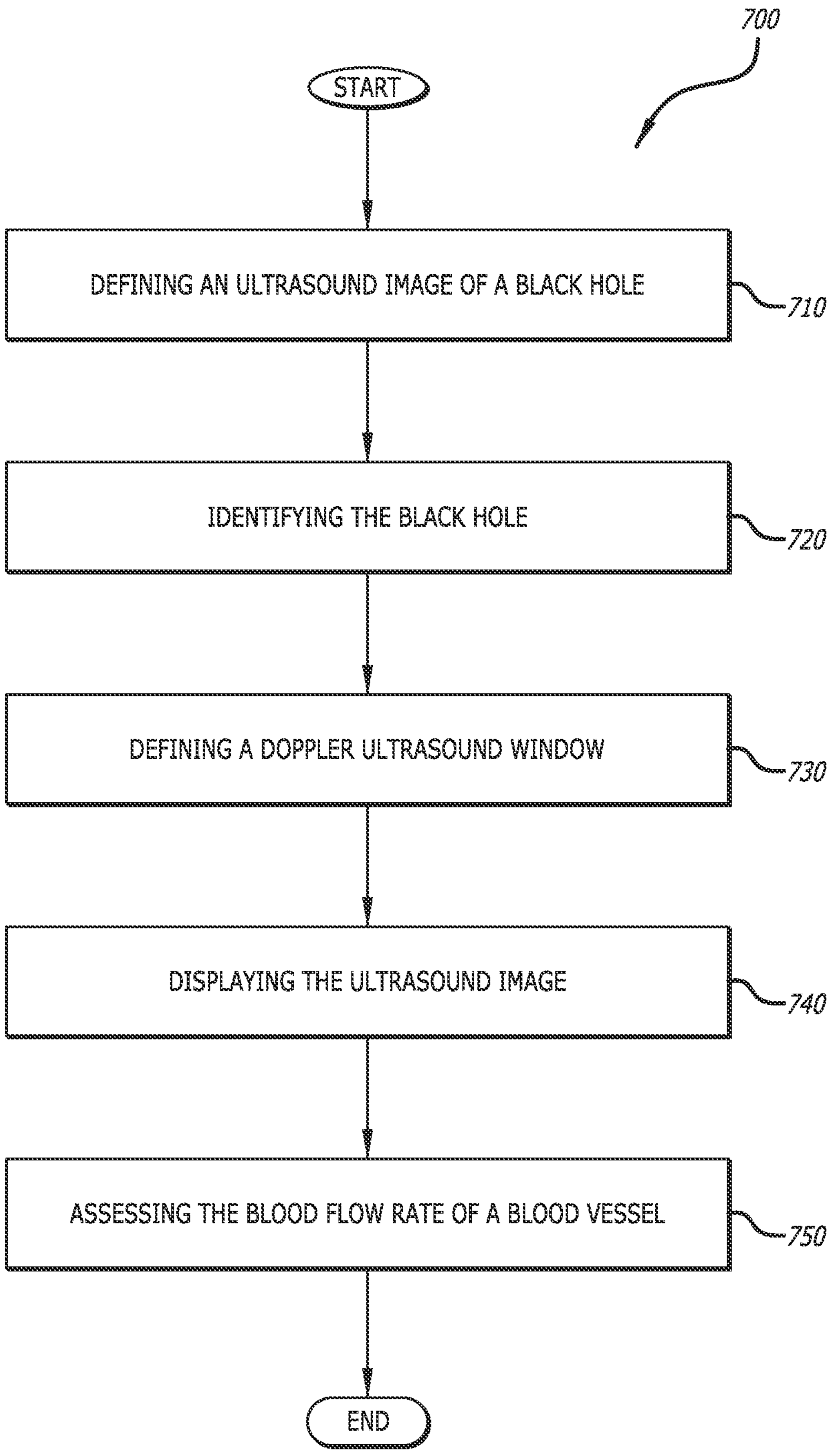
FIG. 7 is a flow chart illustrating operations of a method performed by the system of FIG. 1 in accordance with some embodiments.

FIG. 7 is a flow chart illustrating an exemplary method of the system 100. The method 700 includes operations in accordance with a reference numbers 710-750. The method 700 generally includes defining an ultrasound image including a black hole (block 710).

Defining the ultrasound image may include activating include activating the ultrasonic transducers of the array of the ultrasonic transducers 148 of the ultrasound probe 106 communicatively coupled to the console 102. With the activating operation, the ultrasonic transducers 148 emit generated ultrasound signals into the patient P, receive reflected ultrasound signals from the patient P, and convert the reflected ultrasound signals into corresponding electrical signals for processing into ultrasound images. The activating operations can include activating an approximately linear subset of the ultrasonic transducers 148 of a 2-D array of the ultrasonic transducers 148. Alternatively, the activating operations can include activating a subset of the ultrasonic transducers 148 up to all the ultrasonic transducers 148 in the movable linear array of the ultrasonic transducers 148.

Defining the ultrasound image may further include analyzing ultrasound data to detect black holes within the ultrasound image. In doing so, the logic 120 may analyze ultrasound image data to search for and detect black holes within the predefined target area.

Upon detecting a black hole, the logic 120 may determine an identity of the black hole (block 720). The logic 120 may determine a blood flow condition within the black hole by obtaining doppler ultrasound data. The blood flow condition may include a presence or absence of blood flow. The processing operations may include determining the black hole to be blood vessel. The logic 120 may detect, via doppler ultrasound, a blood flow within the black hole and thereby determine the black hole to be a blood vessel. The logic 120 may further determine a direction of the blood flow with respect to the image plane or more specifically with respect to an orientation of the image plane and thereby, determine the blood vessel to be vein or alternatively an artery. The logic 120 may also detect a non-flow condition of the black hole (i.e., absence of blood flow), and thereby, determine the black hole to be anatomical element other than a blood vessel such as a nerve or a bundle of nerves.

In some embodiments, the processing operations may further determine the blood vessel to be a vein or an artery based on a pulsatility of the blood flow. The logic 120 measure, via doppler ultrasound, a pulsatility of the blood flow within the black hole. As the arterial blood flow is generally more pulsatile than venous blood flow, the logic 120 may compare a measured pulsatility with a predefined pulsatility limit stored in memory. The logic 120 may thereby determine the blood vessel to be (1) an artery if the measured pulsatility exceeds the pulsatility limit or (2) a vein if the measured pulsatility is less than the pulsatility limit.

In some embodiments, the processing operations may further determine the blood vessel to be a vein or an artery based on a spatial positioning of the black hole within the ultrasound image. The logic 120 may compare the ultrasound image with one or more corresponding ultrasound images stored in memory. The logic 120 may more specifically compare the spatial positioning of the black hole within the ultrasound image with the spatial positioning of the corresponding black hole in the one or more corresponding ultrasound images, where the spatial positioning includes a subcutaneous depth of the black hole. As a result of the comparison, the logic 120 may identify the blood vessel as a vein or an artery.

In some embodiments, the processing operations may further include determining a confidence (e.g., a percent probability) for the determined identity of the black hole. The logic 120 may determine the confidence from the determined direction of blood flow, the measured pulsatility of the blood flow, the spatial positioning assessment of the black hole, or any combination thereof. The notification may include a number (e.g., a percent probability) or other confidence indication such as a low, medium, or high level indication of confidence.

The processing operations may further include establishing a doppler ultrasound window (block 730) within the ultrasound image, where the doppler ultrasound window defines a portion of the ultrasound window for assessing blood flow. In some embodiments, the logic 120 automatically may define the doppler ultrasound window to encompass one or more black holes detected within the ultrasound image. According to further embodiments, the logic 120 may receiving an input via an input device as may be entered by a clinician and the logic 120 may define the doppler ultrasound window based on the input. In other words, the clinician may select a portion of the ultrasound image as the doppler ultrasound window and the logic 120 may define the doppler ultrasound window in accordance with the selection.

The displaying operations further include rendering the ultrasound image on the display coupled with the console (block 740). The displaying operations may further include superimposing a visual notification atop the ultrasound image. The notification may indicate the direction of blood flow with respect to the image of the black hole. The logic 120 may cause the notification to be superimposed so as to not obstruct the black hole so that an image of a medical device may superimposed on the ultrasound image over the black hole. The logic 120 may specifically define a boundary or border surrounding the black hole in the ultrasound image. Having defined the boundary, the logic 120 may cause the notification to be superimposed the outside of the boundary. Having identified the black hole to be a vein or an artery, the logic 120 may include the identity of the black hole as a vein or an artery in the notification.

The processing operations may further include assessing the blood flow rate of the blood vessel (block 750). The logic 120 may determine a blood flow rate based on doppler ultrasound data. In some embodiments, the logic 120 may measure a velocity of blood flow across an area of the blood vessel and thereby determine a blood flow rate.

In some embodiments, the logic 120 may compare the measured blood flow rate with a range of blood flow rates for corresponding blood vessels stored in memory. As a result of the comparison, the logic 120 may determine that the blood flow within the blood vessel is compromised, e.g., low with respect to the range of blood flow rates. As a result of the comparison, the logic 120 may determine that the blood vessel is partially and/or totally occluded.

In some embodiments, the logic 120 may obtain a first blood flow rate measurement for the blood vessel and subsequently obtain a second blood flow rate measurement. The logic 120 may then comparing the second measurement with the first measurement and determine from the comparison that the blood flow rate is compromised when blood flow rate of the second measurement is less than the blood flow rate of the first measurement. In some instances, the second measurement may be obtained at a second location along the blood vessel different from a first location of the first measurement.

Other methods may include magnetic signal-related operations. The magnetic signal-related operations can include a converting operation. The converting operation includes converting magnetic signals from a magnetized medical device (e.g., the needle 112) with the magnetic-sensor array 146 of the ultrasound probe 106 into corresponding electrical signals. The processing operations further include processing the corresponding electrical signals of the magnetic signals with the processor 116 into distance and orientation information with respect to the predefined target area. The displaying operations further include displaying an iconographic representation of the medical device on the display screen 104. In some embodiments, the logic 120 may define the doppler ultrasound window based on the location of the iconographic representation of the medical device in relation to the ultrasound image.

Other methods may further include a number of optical signal-related operations in combination with further processing and displaying operations. The optical signal-related operations include emitting input optical signals, receiving reflected optical signals, and converting the reflected optical signals into corresponding electrical signals of the optical signals by the optical interrogator 154. The optical signal-related operations also include conveying the input optical signals from the optical interrogator 154 to the number of FBG sensors along the length of the optical-fiber stylet 156, as well as conveying the reflected optical signals from the number of FBG sensors back to the optical interrogator 154 with the optical-fiber stylet 156 disposed in a lumen of the medical device. The processing operation further include processing the corresponding electrical signals of the optical signals with the processor 116 into distance and orientation information with respect to the predefined target area. The displaying operations further include displaying an iconographic representation of a medical device on the display screen 104.

Other method operations can include a data-providing operation in combination with further processing operations. The data-providing operation includes providing positional-tracking data to the console 102 from the accelerometer 160, the gyroscope 162, the magnetometer 164, or a combination thereof of the ultrasound probe 106. The processing operations further include processing the positional-tracking data with the processor 116.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound-imaging system, comprising:

an ultrasound probe including an array of ultrasonic transducers, activated ultrasonic transducers of the array of ultrasonic transducers configured to emit generated ultrasound signals into a patient, receive reflected ultrasound signals from the patient, and convert the reflected ultrasound signals into corresponding electrical signals for processing into ultrasound image data and doppler ultrasound data; and a console configured to communicate with the ultrasound probe, the console including one or more processors and a non-transitory computer-readable medium having stored thereon logic, when executed by the one or more processors, causes operations including:

detecting a black hole within a predefined target area of the patient based on ultrasound image data;

determining a blood flow condition within the black hole based at least partially on doppler ultrasound data;

defining an ultrasound image of the predefined target area including an image of the black hole;

identifying the black hole as a blood vessel by comparing the ultrasound image with one or more corresponding ultrasound images stored in memory; and superimposing a notification atop the ultrasound image, wherein the notification indicates the blood flow condition within the black hole;

identifying the blood vessel as a vein or alternatively as an artery; and identifying the blood vessel as the vein or the artery based at least partially on the blood flow condition within the blood vessel.

2. The ultrasound-imaging system of claim 1, wherein:

the operations further include determining a direction of blood flow within the black hole with respect to an image plane of the ultrasound image, and the notification indicates the direction of blood flow with respect to the image of the black hole.

3. The ultrasound-imaging system of claim 1, wherein the notification does not obstruct the image of the black hole.

4. The ultrasound-imaging system of claim 1, wherein the operations further include:

defining a boundary surrounding the image of the black hole; and superimposing the notification outside of the boundary.

5. The ultrasound-imaging system of claim 1, wherein the operations further include rendering the ultrasound image on a display coupled with the console.

6. The ultrasound-imaging system of claim 1, wherein the operations further include identifying the blood vessel as the vein or alternatively as the artery based at least partially on a direction of the blood flow with respect to an image plane.

7. The ultrasound-imaging system of claim 1, wherein the operations further include:

measuring a pulsatility of the blood flow via doppler ultrasound; and identifying the blood vessel as the vein or the artery based at least partially on measuring the pulsatility.

8. The ultrasound-imaging system of claim 1, wherein the operations further include:

comparing the ultrasound image with one or more corresponding ultrasound images stored in memory, the comparing including a comparison of spatial positioning of the blood vessel within the ultrasound image; and identifying the blood vessel as the vein or as the artery at least partially as a result of the comparison.

9. The ultrasound-imaging system of claim 1, wherein the notification further indicates an identity of the blood vessel as the vein or as the artery.

10. The ultrasound-imaging system of claim 1, wherein:

the operations further include determining a confidence for an identification of the blood vessel, and the notification further indicates the confidence for the identification of the blood vessel.

11. The ultrasound-imaging system of claim 1, wherein the operations further include:

measuring a blood flow rate within the blood vessel;

comparing the blood flow rate with a range of blood flow rates stored in memory; and as a result of the comparing, determining that the blood flow rate within the blood vessel is compromised.

12. The ultrasound-imaging system of claim 11, wherein the operations further include, as a result of the comparing, determining that the blood vessel is partially and/or totally occluded.

13. The ultrasound-imaging system of claim 1, wherein the operations further include:

obtaining a first blood flow rate measurement for the blood vessel;

obtaining a second blood flow rate measurement for the blood vessel, the second blood flow rate measurement subsequent to the first blood flow rate measurement;

comparing the second blood flow rate measurement with the first blood flow rate measurement; and as a result of comparing the first and the second flow rate measurement, determining that a blood flow rate within the blood vessel is compromised.

14. The ultrasound-imaging system of claim 1, wherein the operations further include:

detecting a plurality of black holes within the predefined target area of the patient based on ultrasound image data;

determining the blood flow condition within each of the plurality of black holes based at least partially on doppler ultrasound data; and identifying each of the plurality of black holes as a blood vessel or alternatively as one or more nerves, wherein identifying a black hole as one or more nerves includes determining a non-flow condition of blood within the respective black hole.

15. The ultrasound-imaging system of claim 1, wherein the operations further include:

defining a doppler ultrasound window extending at least partially across the ultrasound image, the doppler ultrasound window encompassing one or more black holes; and determining the blood flow condition within each of the one or more black holes encompassed by the doppler ultrasound window based on doppler ultrasound data.

16. The ultrasound-imaging system of claim 15, wherein defining the doppler ultrasound window includes:

detecting the one or more black holes based on the ultrasound image data; and automatically defining the doppler ultrasound window to encompass the one or more black holes.

17. The ultrasound-imaging system of claim 15, wherein defining the doppler ultrasound window includes:

receiving an input via an input device of the ultrasound-imaging system; and defining the doppler ultrasound window based on the input, wherein the input includes a selected portion of the ultrasound image.

18. The ultrasound-imaging system of claim 1, the ultrasound probe further comprising: an array of magnetic sensors configured to convert magnetic signals from a magnetized medical device into corresponding electrical signals of the magnetic signals for processing by the one or more processors into distance and orientation information with respect to the predefined target area for rendering of an iconographic representation of the magnetized medical device atop the ultrasound image.

19. The ultrasound-imaging system of claim 18, wherein defining the doppler ultrasound window is based on a position of the iconographic representation of the magnetized medical device atop the ultrasound image.

20. An ultrasound-imaging system, comprising:

an ultrasound probe including an array of ultrasonic transducers, activated ultrasonic transducers of the array of ultrasonic transducers configured to emit generated ultrasound signals into a patient, receive reflected ultrasound signals from the patient, and convert the reflected ultrasound signals into corresponding electrical signals for processing into ultrasound image data and doppler ultrasound data; and a console configured to communicate with the ultrasound probe, the console including one or more processors and a non-transitory computer-readable medium having stored thereon logic, when executed by the one or more processors, causes operations including:

detecting a black hole within a predefined target area of the patient based on ultrasound image data;

determining a blood flow condition within the black hole based at least partially on doppler ultrasound data;

defining an ultrasound image of the predefined target area including an image of the black hole;

identifying the black hole as a blood vessel by comparing the ultrasound image with one or more corresponding ultrasound images stored in memory;

superimposing a notification atop the ultrasound image, wherein the notification indicates the blood flow condition within the black hole;

detecting a plurality of black holes within the predefined target area of the patient based on ultrasound image data;

determining a blood flow condition within each of the plurality of black holes based at least partially on doppler ultrasound data; and identifying each of the plurality of black holes as a blood vessel or alternatively as one or more nerves, wherein identifying a black hole as one or more nerves includes determining a non-flow condition of blood within the respective black hole.

21. An ultrasound-imaging system, comprising:

an ultrasound probe including:

an array of ultrasonic transducers, activated ultrasonic transducers of the array of ultrasonic transducers configured to emit generated ultrasound signals into a patient, receive reflected ultrasound signals from the patient, and convert the reflected ultrasound signals into corresponding electrical signals for processing into ultrasound image data and doppler ultrasound data; and an array of magnetic sensors configured to convert magnetic signals from a magnetized medical device into corresponding electrical signals of the magnetic signals for processing by the one or more processors into distance and orientation information with respect to a predefined target area for rendering of an iconographic representation of the magnetized medical device atop the ultrasound image data; and a console configured to communicate with the ultrasound probe, the console including one or more processors and a non-transitory computer-readable medium having stored thereon logic, when executed by the one or more processors, causes operations including:

detecting a black hole within a predefined target area of the patient based on ultrasound image data;

determining a blood flow condition within the black hole based at least partially on doppler ultrasound data;

defining an ultrasound image of the predefined target area including an image of the black hole;

identifying the black hole as a blood vessel by comparing the ultrasound image with one or more corresponding ultrasound images stored in memory; and superimposing a notification atop the ultrasound image, wherein the notification indicates the blood flow condition within the black hole.

22. The ultrasound-imaging system of claim 21, wherein defining a doppler ultrasound window is based on a position of the iconographic representation of the magnetized medical device atop the ultrasound image.

* * * * *